US007615529B2

(12) United States Patent
Kong-Beltran et al.

(10) Patent No.: US 7,615,529 B2
(45) Date of Patent: Nov. 10, 2009

(54) METHODS AND COMPOSITIONS FOR MODULATING HYPERSTABILIZED C-MET

(75) Inventors: Monica Kong-Beltran, San Mateo, CA (US); Dineli M. Wickramasinghe, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 66 days.

(21) Appl. No.: 11/388,757

(22) Filed: Mar. 24, 2006

(65) Prior Publication Data

US 2006/0270594 A1    Nov. 30, 2006

Related U.S. Application Data

(60) Provisional application No. 60/665,482, filed on Mar. 25, 2005.

(51) Int. Cl.
*A01N 37/18* (2006.01)
*G01N 33/566* (2006.01)
*C12Q 1/68* (2006.01)
*C07K 16/00* (2006.01)
*C12P 21/08* (2006.01)

(52) U.S. Cl. .............................. 514/2; 435/6; 436/501; 530/387.9; 530/388.1; 530/388.15; 530/388.22; 536/24.31

(58) Field of Classification Search ............... 435/6, 435/91.1, 91.31, 455; 530/300, 350, 387.1, 530/387.9, 388.1, 388.15, 388.22; 536/23.1, 536/24.31; 424/9.1; 436/501; 514/1, 2
See application file for complete search history.

(56) References Cited

U.S. PATENT DOCUMENTS

| 6,099,841 | A | 8/2000 | Hillan et al. |
| 2005/0037431 | A1* | 2/2005 | Kirchhofer et al. ............ 435/7.1 |
| 2005/0042216 | A1 | 2/2005 | Frantz et al. |
| 2005/0233960 | A1* | 10/2005 | Kong-Beltran et al. ........ 514/12 |
| 2006/0263808 | A1 | 11/2006 | Yauch |
| 2006/0270594 | A1 | 11/2006 | Kong-Beltran et al. |

FOREIGN PATENT DOCUMENTS

| WO | WO 96/38557 | 12/1996 |
| WO | 97/38125 | 10/1997 |
| WO | WO 2004/072117 | 8/2004 |
| WO | WO 2005/016382 | 2/2005 |
| WO | WO 2005/063816 A2 | 7/2005 |
| WO | 2006/104912 | 10/2006 |

OTHER PUBLICATIONS

A. Peracchi et al, Rev. Med. Virol., 14: 47-64 (2004).*
A. Branch, Trends in Biochem. Sci. 23: 45-50 (1998).*
S. Crooke, Antisense Res. and Application, Chapter 1, pp. 1-50 (1998).*
S.R. Hubbard, Nature Rev. Mol. Cell. Biol., vol. 5, pp. 464-471 (2004).*
Opalinska et al, Nature Rev., 1: 503-514 (2004).*
S. Agrawal et al., Molecular Med. Today, 6: 72-81 (2000).*
Chirila et al., Biomaterials, 23: 321-342 (2002).*
Peschard et al, Mol. Cell, vol. 8, pp. 995-1004 (2001).*
"European Patent Office search" (Apr. 30, 2008).
"SGX Drug Discovery and Development [online] URL:http://www.sgxpharma.com/pipeline/documents/SGX_echeminfo_10172007_Final.pdf [retrieved on Mar. 28, 2008]" *SGX Pharmaceuticals* pp. 1-27 (Mar. 2008).
Dietrich, Sascha, et al., "Role of c-MET in Upper Aerodigestive Malignancies—From Biology to Novel Therapies" *J. of Environmental Pathology, Toxicology and Oncology* 24(3):149-162 (2005).
Liu, Youhua, "The human hepatocyte growth factor receptor gene: complete structural organization and promoter characterization1" *Gene* 215:159-169 (1998).
Lynch et al., "Activating Mutations in the Epidermal Growth Factor Receptor Underlying Responsiveness of Non-Small-Cell Lung Cancer to Gefitinib" *New England J. of Medicine* 350(21):2129-2139 (May 20, 2004).
Ma Patrick C. et al., "c-Met: Structure, functions and potential for therapeutic inhibition" *Cancer and Metastasis Reviews* 22(4):309-325 (Dec. 2003).
NCBI, "Database NCBI [online] Accession No. rs35225896 Aug. 10, 2005".
Paez et al., "EGFR Mutations in Lung Cancer, Correlation with Clinical Response to Gefitinib Therapy" *Science* 304:1497-1500 (Jun. 4, 2004).
Pao et al., "EGF receptor gene mutations are common in lung cancers from "never smokers" and are associated with sensitivity of tumors to gefitinib and erlotinib" *Proc. Natl. Acad. Sci. USA* 101(36):13306-13311 (Sep. 7, 2004).
Serra et al., "Somatic NF1mutational spectrum in benign neurofibromas:mRNA splice defects are common among point mutations" *Hum Genet* 108:416-429 (May 8, 2001).
Sordella et al., "Gefitinib-Sensitizing EGFR Mutations in Lung Cancer Activate Anti-Apoptotic Pathways" *Science* 305:1163-1167 (Aug. 20, 2004).
Tockman et al., "Considerations in Bringing a Cancer Biomarker to Clinical Application" *Cancer Research* 52:2711s-2718s (May 1, 1992).
Baek et al., "Transforming variant of Met receptor confers serum independence and anti-apoptotic property and could be involved in the mouse thymic lymphomagenesis" *Experimental and Molecular Medicine* 36(4):283-291 (Aug. 2004).
Bardelli et al., "Gab1 Coupling to the HGF/Met Receptor Multifunctional Docking Site Requires Binding of Grb2 and Correlates with the Transforming Potential" *Oncogene* 15:3103-3111 (1997).
Birchmeier et al., "Met, Metastasis, Motility and More" *Nature Reviews Molecular Cell Biology* 4:915-925 (Dec. 2003).
Bladt et al., "Essential Role for the C-met Receptor in the Migration of Myogenic Precursor Cells into the Limb Bud" *Nature* 376:768-770 (Aug. 31, 1995).
Boix et al., "C-Met mRNA Overexpression in Human Hepatocellular Carcimoma" *Hepatology* 19(1):88-91 (Jan. 1994).

(Continued)

*Primary Examiner*—Jane Zara
(74) *Attorney, Agent, or Firm*—Cara M. Coburn

(57) ABSTRACT

The invention provides methods and compositions for modulating the HGF/c-met signaling pathway, in particular by inhibiting a hyperstabilized c-met protein.

7 Claims, 11 Drawing Sheets

OTHER PUBLICATIONS

Bussolino et al., "Hepatocyte Growth Factor is a Potent Angiogenic Factor Which Stimulates Endothelial Cell Motility and Growth" *Journal of Cell Biology* 119(3):629-641 (Nov. 1992).

Cooper et al., "Molecular cloning of a new transforming gene from a chemically transformed human cell line" *Nature* 311:29-33 (Sep. 6, 1984).

Danilkovitch-Miagkova & Zbar, "Dysregulation of Met receptor tyrosine kinase activity in invasive tumors" *The Journal of Clinical Investigation* 109(7):863-867 (Apr. 2002).

Di Renzo et al., "Overexpression and Amplification of the Met/HGF Receptor Gene During the Progression of Colorectal Cancer" *Clinical Cancer Research* 1:147-154 (Feb. 1995).

Elliott et al., "The role of hepatocyte growth factor (scatter factor) in epithelial-mesenchymal transition and breast cancer" *Can. J. Physiol. Pharmacol.* 80:91-102 (Feb. 2002).

Furge et al., "Met Receptor Tyrosine Kinase: Enhanced Signaling Through Adapter Proteins" *Oncogene* 19:5582-5589 (2000).

Gherardi et al., "Functional map and domain structure of MET, the product of the c-met protooncogene and receptor for hepatocyte growth factor/scatter factor" *Proc. Natl. Acad. Sci. USA* 100(21):12039-12044 (Oct. 14, 2003).

Giordano et al., "Different Point Mutations in the MET Oncogene Elicit Distinct Biological Properties" *The Faseb Journal* 14:399-406 (Feb. 2000).

Giordano et al., "The Semaphorin 4D Receptor Controls Invasive Growth by Coupling with MET" *Nature Cell Biology* 4:720-724 (Sep. 2002).

Hartmann et al., "The Motility Signal of Scatter Factor/Hepatocyte Growth Factor Mediated Through the Receptor Tyrosine Kinase Met Requires Intracellular Action of Ras" *Journal of Biological Chemistry* 269(35):21936-21939 (Sep. 2, 1994).

Heinrich et al., "PDGFRA activating mutations in gastrointestinal stromal tumors" *Science* 299(5607):708-710 (Jan. 31, 2003).

Hirota et al., "Gain-of-function mutations of c-kit in human gastrointestinal stromal tumors" *Science* 279(5350):577-580 (Jan. 23, 1998).

Hubbard, "Juxtamembrane autoinhibition in receptor tyrosine kinases." *Nature Rev Mol Cell Bio.* 5:464-470 (Jun. 2004).

Jeffers et al., "Activating Mutations for the Met Tyrosine Kinase Receptor in Human Cancer" *Proc. Natl. Acad. Sci. USA* 94:11445-11450 (Oct. 1997).

Jeffers et al., "Degradation of the Met Tyrosine Kinase Receptor by the Ubiquitin-Proteasome Pathway" *Molecular & Cellular Biology* 17(2):799-808 (Feb. 1997).

Jeffers et al., "Enhanced Tumorigenicity and Invasion-Metastasis by Hepatocyte Growth Factor/Scatter Factor-met Signaling in Human Cells Concomittant with Induction fo the Urokinase Proteolysis Network" *Molecular & Cellular Biology* 16(3):1115-1125 (Mar. 1996).

Jin et al., "Expression of Scatter Factor and C-Met Receptor in Benign and Malignant Breast Tissue" *Cancer* 79(4):749-760 (Feb. 15, 1997).

Kong-Beltran et al., "Somatic mutations lead to an oncogenic deletion of met in lung cancer" *Cancer Research* 66(1):283-289 (Jan. 1, 2006).

Kong-Beltran M et al., "The Sema domain of Met is necessary for receptor dimerization and activation" *Cancer Cell* 6(1):75-84 (Jul. 2004).

Kuniyasu et al., "Aberrant Expression of C-met mRNA in Human Gastric Carcinomas" *Int. J. Cancer* 55:72-75 (1993).

Lee et al., "Identification of a Novel Type of Alternative Splicing of a Tyrosine Kinase Receptor" *Journal of Biological Chemistry* 269(30):19457-19461 (Jul. 29, 1994).

Liu et al., "Overexpression of C-met Proto-Oncogene But Not Epidermal Growth Factor Receptor or C-erbB-2 in Primary Human Colorectal Carcinomas" *Oncogene* 7:181-185 (1992).

Lorenzato et al., "Novel Somatic Mutations of the MET Oncogene in Human Carcinoma Metastases Activating Cell Motility and Invasion" *Cancer Research* 62:7025-7030 (Dec. 1, 2002).

Ma et al., "c-MET Mutational Analysis in Small Cell Lung Cancer: Novel Juxtamembrane Domain Mutations Regulating Cytoskeletal Functions" *Cancer Research* 63:6272-6281 (Oct. 1, 2003).

Ma et al., "Circulating Tumor Cells and Serum Tumor Biomarkers in Small Cell Lung Cancer" *Anticancer Research* 23:49-62 (2003).

Ma et al., "Functional Expression and Mutations of c-Met and Its Therapeutic Inhibition with SU11274 and Small Interfering RNA in Non-Small Cell Lung Cancer" *Cancer Research* 65(4):1479-1488 (Feb. 15, 2005).

Maina et al., "Uncoupling of Grb2 from the Met Receptor in Vivo Reveals Complex Roles in Muscle Development" *Cell* 87:531-542 (Nov. 1, 1996).

Marmor et al., "Role of protein ubiquitylation in regulating endocytosis of receptor tyrosine kinases" *Oncogene* 23:2057-2070 (2004).

Matsumoto et al., "Roles of HGF as a pleiotropic factor in organ regeneration" *Exs* 65:225-249 (1993).

Maulik et al., "Role of the hepatocyte growth factor receptor, c-Met, in oncogenesis and potential for therapeutic inhibition" *Cytokine & Growth Factor Reviews* 13:41-59 (2002).

Meiners et al., "Role of Morphogenetic Factors in Metastasis of Mammary Carcinoma Cells" *Oncogene* 16:9-20 (1998).

Morello et al., "MET Receptor is Overexpressed but not Mutated in Oral Squamous Cell Carcinomas" *Journal of Cellular Physiology* 189:285-290 (2001).

Nakao et al., "Internal tandem duplication of the flt3 gene found in acute myeloid leukemia" *Leukemia* 10(12):1911-1918 (Dec. 1996).

Natali et al., "Overexpression of the Met/HGF Receptor in Renal Cell Carcinomas" *Int. J. Cancer* 69:212-217 (1996).

Nguyen et al., "Association of the Multisubstrate Docking Protein Gab1 with the Hepatocyte Growth Factor Receptor Requires a Functional Grb2 Binding Site Involving Tyrosine 1356" *Journal of Biological Chemistry* 272(33):20811-20819 (Aug. 15, 1997).

Nusrat et al., "Hepatocyte Growth Factor/Scatter Factor Effects on Epithelia. Regulation of Intercellular Junctions in Transformed and Natural Intestinal Epithelia . . . " *J. Clin. Invest.* 93:2056-2065 (May 1994).

Ohashi et al., "Sustained survival of human hepatocytes in mice: A model for in vivo infection with human hepatitis B and hepatitis delta viruses" *Nature Medicine* 6(3):327-331 (Mar. 2000).

Olivero et al., "Novel Mutation in the ATP-Binding Site of the MET Oncogen Tyrosine Kinase in a HPRCC Family" *Int. J. Cancer* 82:640-643 (1999).

Olivero et al., "Overexpression and Activation of Hepatocyte Growth Factor/Scatter Factor in Human Non-Small-Cell Lung Carcinomas" *Br. J. Cancer* 74:1862-1868 (1996).

Orian-Rousseau et al., "CD44 is Required for two Consecutive Steps in HGF/c-MET Signaling" *Genes & Development* 16:3074-3086 (2002).

Park et al., "Mechanism of Met Oncogene Activation" *Cell* 45:895-904 (Jun. 20, 1986).

Pelicci et al., "The Motogenic and Mitogenic Responses to HGF are Amplified by the Shc Adaptor Protein" *Oncogene* 10:1631-1638 (1995).

Peschard et al., "A Conserved DpYR Motif in the Juxtamembrane Domain of the Met Receptor Family Forms an Atypical c-Cbl/Cbl-b Tyrosine Kinase Binding Domain Binding Site Required for Suppression of Oncogenic Activation" *Journal of Biological Chemistry* 279(28):29565-29571 (Jul. 9, 2004).

Peschard et al., "Escape from Cbl-mediated downregulation: A recurrent theme for oncogenic deregulation of receptor tyrosine kinases" *Cancer Cell* 3:519-523 (Jun. 2003).

Peschard et al., "Mutation of the c-Cbl TKB Domain Binding Site on the Met Receptor Tyrosine Kinase Converts It into a Transforming Protein" *Molecular Cell.* 8:995-1004 (Nov. 2001).

Petrelli et al., "The endophilin-CIN85-Cbl complex mediates ligand-dependent downregulation of c-Met" *Nature* 416:187-190 (Mar. 14, 2002).

Ponzetto et al., "A Multifunctional Docking Site Mediates Signaling and Transformation by the Hepatocyte Growth Factor/Scatter Factor Receptor Family" *Cell* 77:261-271 (Apr. 22, 1994).

Ponzetto et al., "Specific Uncoupling of GRB2 from the Met Receptor. Differential Effects on Transformation and Motility" *Journal of Biological Chemistry* 271(24):14119-14123 (Jun. 14, 1996).

Royal et al., "Hepatocyte Growth Factor-Induced Scatter of Madin-Darby Canine Kidney Cells Requires Phosphatidylinositol 3-Kinase" *Journal of Biological Chemistry* 270(46):27780-27787 (Nov. 17, 1995).

Schmidt et al., "Germline and Somatic Mutations in the Tyrosine Kinase Domain of the MET Proto-oncogene in Papillary Renal Carcinomas" *Nature Genetics* 16:68-73 (May 1997).

Schmidt et al., "Novel Mutations of the MET Proto-oncogene in Papillary Renal Carcinomas" *Oncogene* 18:2343-2350 (1999).

Schmidt et al., "Scatter factor/hepatocyte growth factor is essential for liver development" *Nature* 373:699-702 (Feb. 23, 1995).

Schwall et al., "Inhibition of cMet activation by a one-armed antibody" *Proceedings of the American Association for Cancer Research* (Abstract #1424) 45:327 (Mar. 2004).

Seidel et al., "Role of hepatocyte growth factor and its receptor c-met in multiple myeloma" *Medical Oncology* 15:145-153 (Sep. 1998).

Shtiegman et al., "The role of ubiquitylation in signaling by growth factors: implications to cancer" *Seminars in Cancer Biology* 13:29-40 (2003).

Siegfried et al., "The Clinical Significance of Hepatocyte Growth Factor for Non-Small Cell Lung Cancer" *Ann Thorac Surg.* 66:1915-1918 (1998).

Tempest et al., "Structure of the Met Protein and Variation of Met Protein Kinase Activity Among Human Tumour Cell Lines" *Br. J. Cancer* 58(1):3-7 (Jul. 1988).

Trusolino & Comoglio, "Scatter-Factor and Semaphorin Receptors: Cell Signalling for Invasive Growth" *Nature Rev. Cancer* 2:289-300 (Apr. 2002).

Trusolino et al., "A Signaling Adapter Function for Alpha6beta4 Integrin in the Control of HGF-Dependent Invasive Growth" *Cell* 107:643-654 (Nov. 30, 2001).

Uehara et al., "Placental defect and embryonic lethality in mice lacking hepatocyte growth factor/scatter factor" *Nature* 373:702-705 (Feb. 23, 1995).

Van Vactor et al., "Neural Developmlent: The Semantics of Axon Guidance" *Current Biology* 9(6):R201-204 (1999).

Wang et al., "Activation of the Met Receptor by Cell Attachment Induces and Sustains Hepatocellular Carcinomas in Transgenic Mice" *Journal Cell Biology* 153(5):1023-1033 (May 28, 2001).

Weidner et al., "Interaction Between Gab1 and the C-Met Receptor Tyrosine Kinase is Responsible for Epithelial Morphogenesis" *Nature* 384:173-176 (Nov. 14, 1996).

"International Preliminary Report on Patentability for International Patent Application No. PCT/US2006/010851 dated Sep. 25, 2007".

"International Preliminary Report on Patentability for International Patent Application PCT/US2006/010850, dated Sep. 25, 2007".

"International Search Report and Written Opinion for International Patent Application No. PCT/US2006/010850 dated Dec. 28, 2006".

"International Search Report for International Patent Application No. PCT/US2006/010851 dated Oct. 5, 2006".

"Office Action mailed Aug. 8, 2008 in U.S. Appl. No. 11/388,773".

"Office Action mailed Oct. 16, 2007 in U.S. Appl. No. 11/388,773."

\* cited by examiner

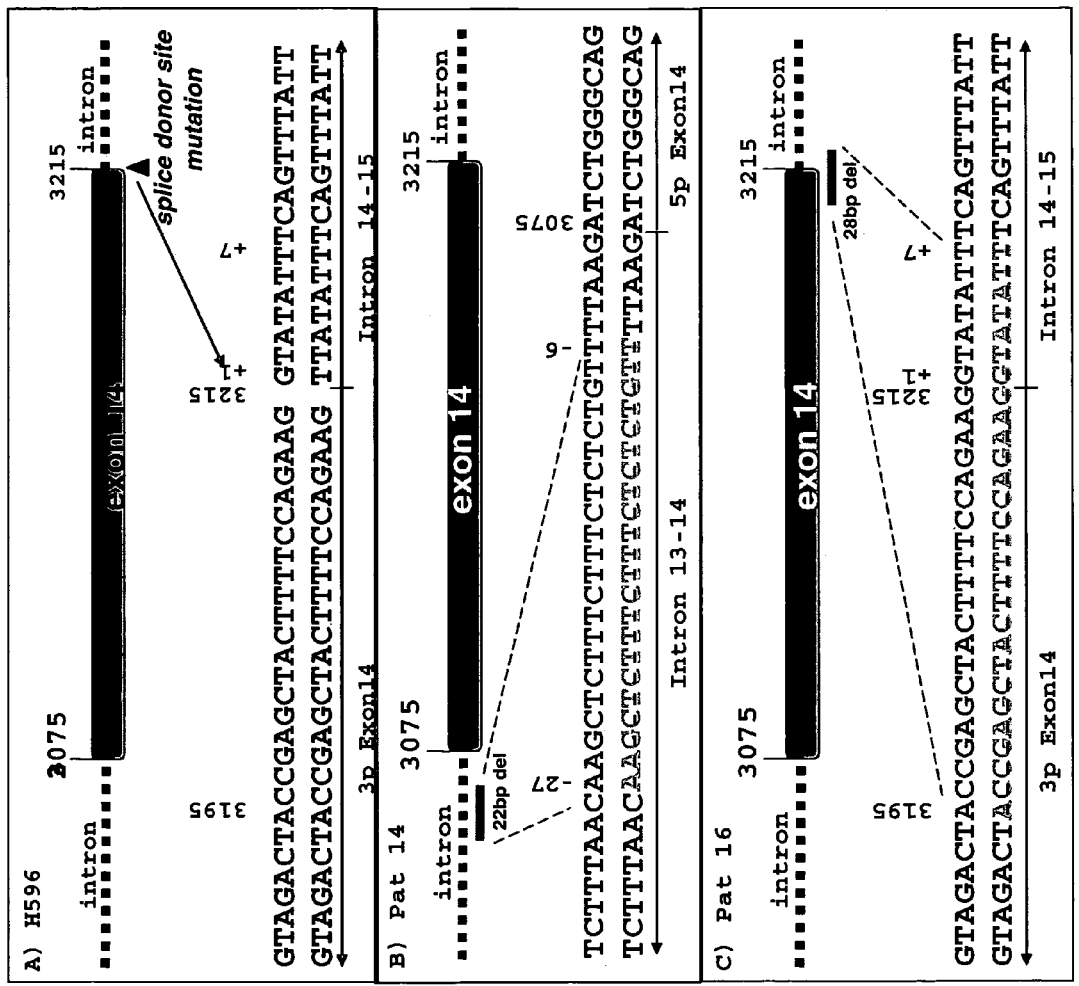
FIG._1

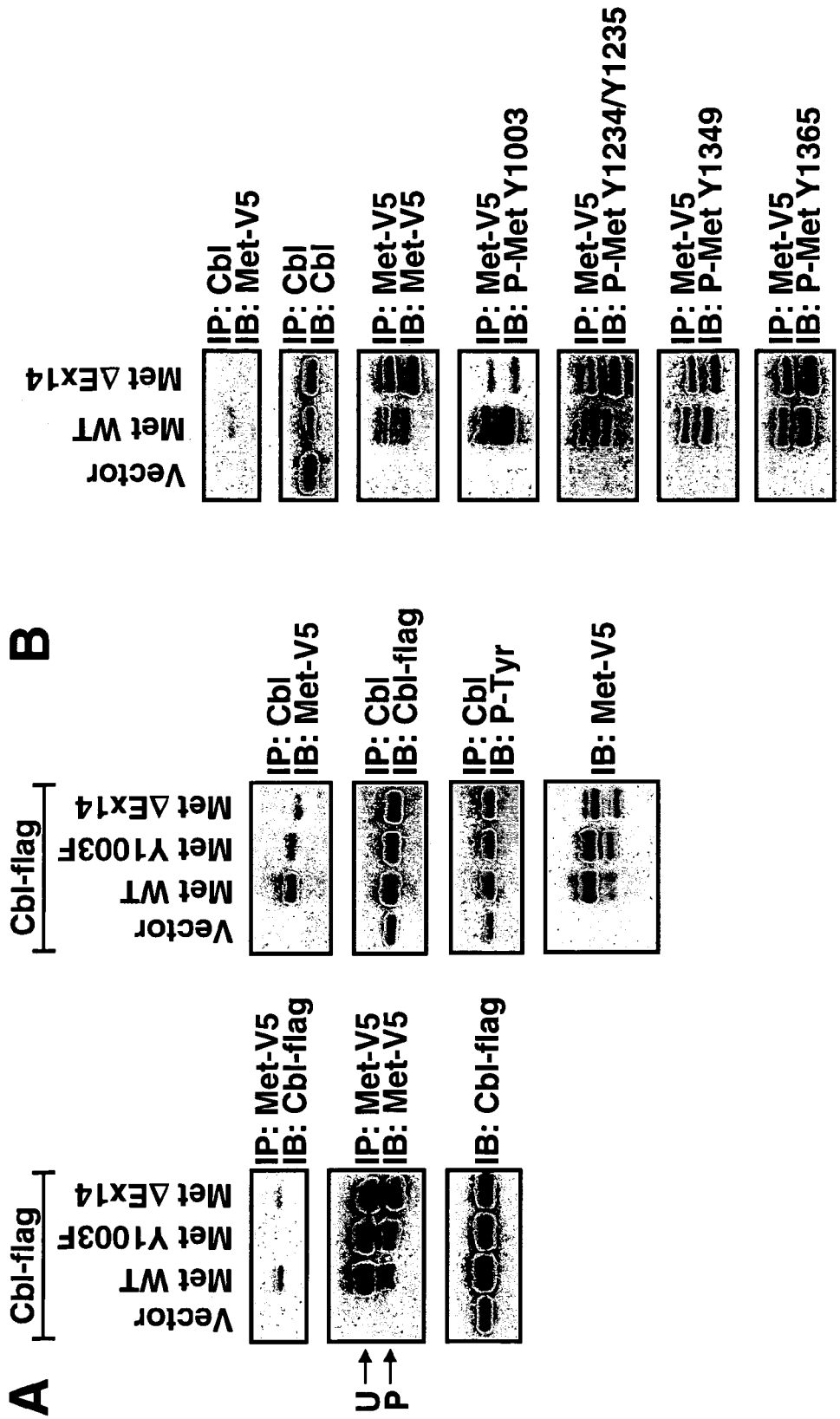
FIG._2A
FIG._2B

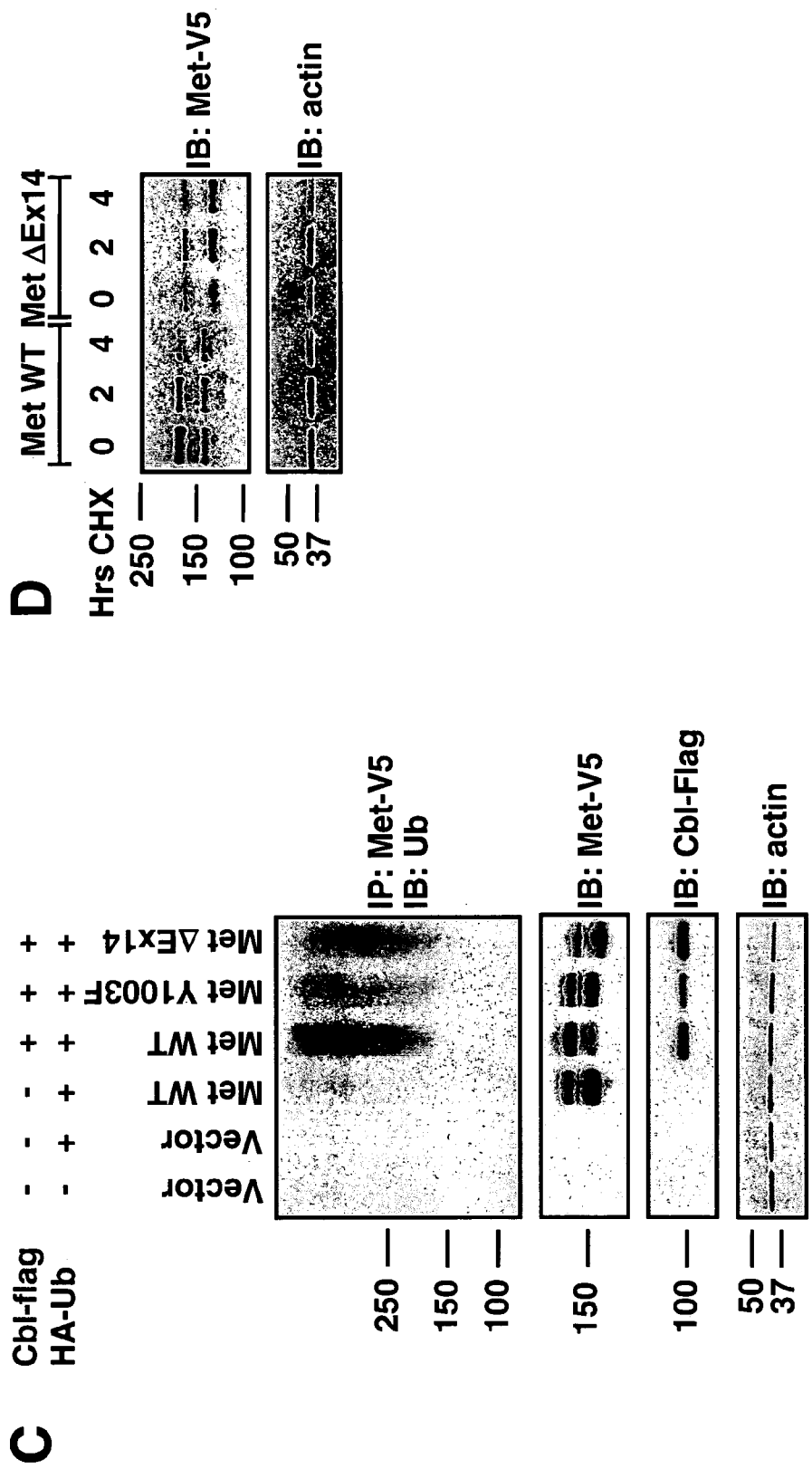
FIG._2D
FIG._2C

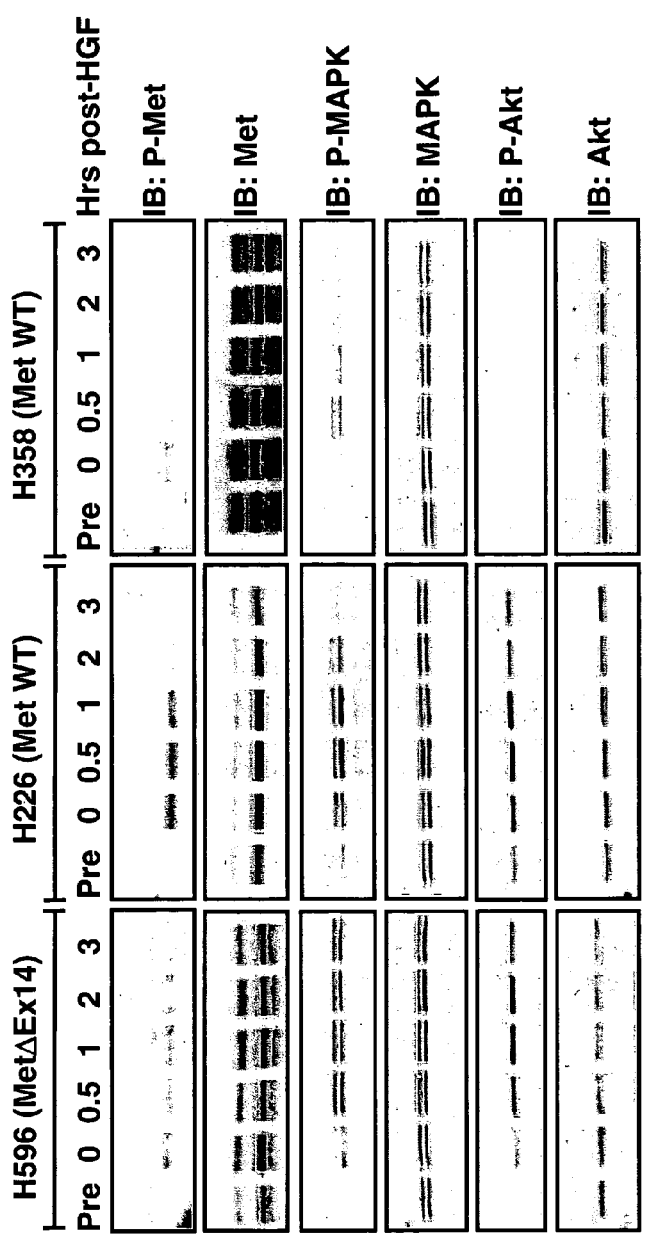
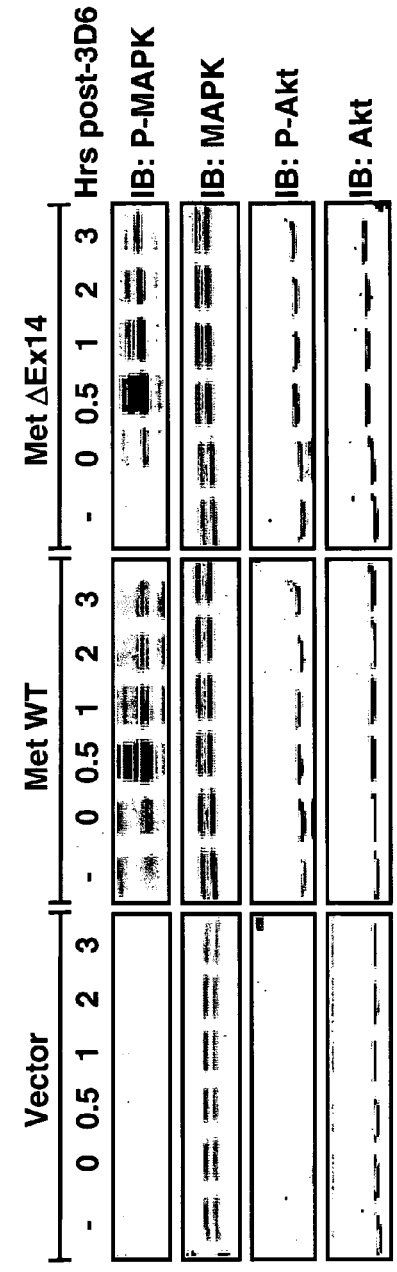
FIG._2E
FIG._2F

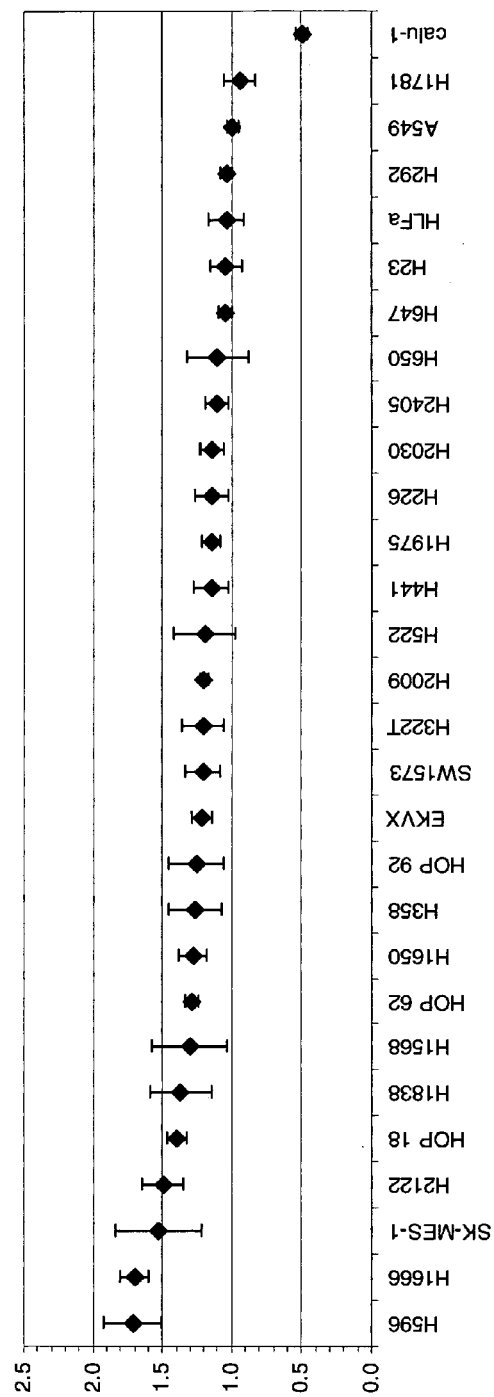
FIG._3A
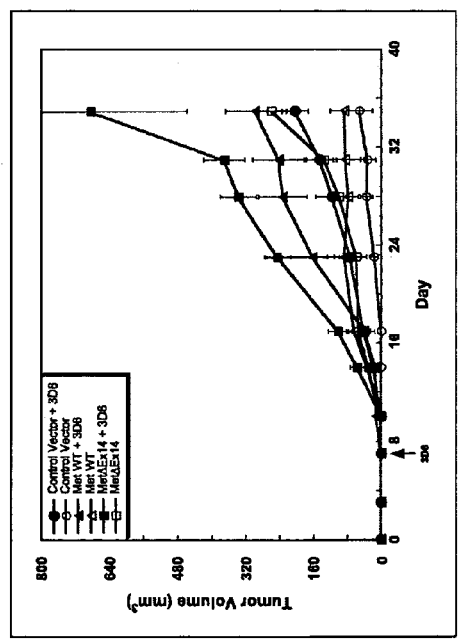
FIG._3B

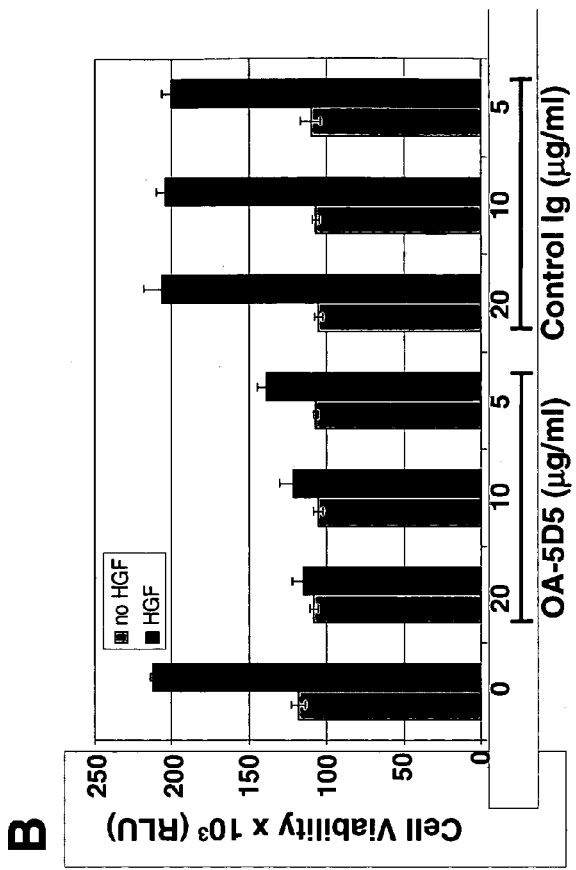
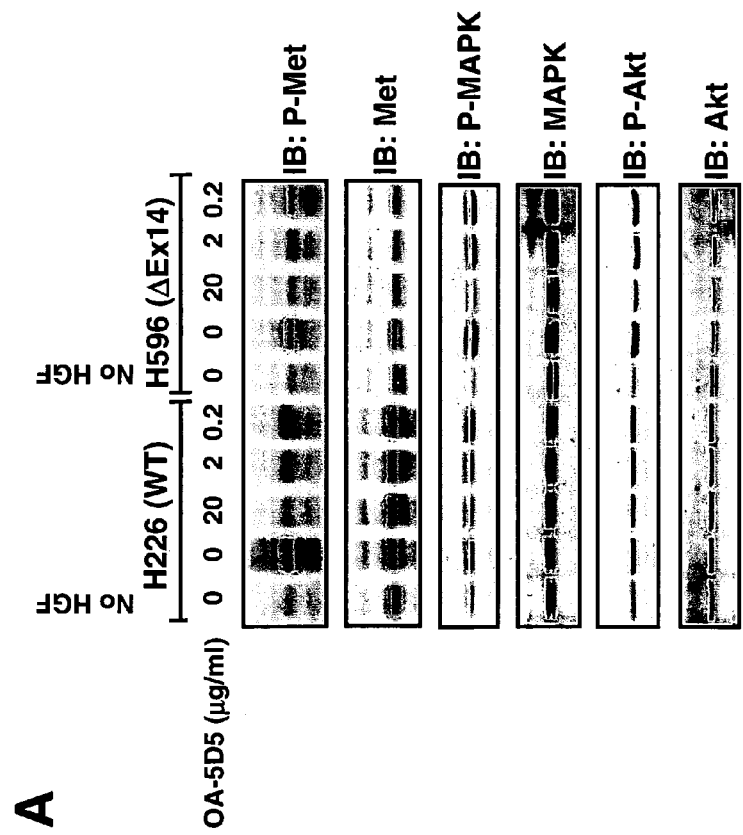
FIG._4

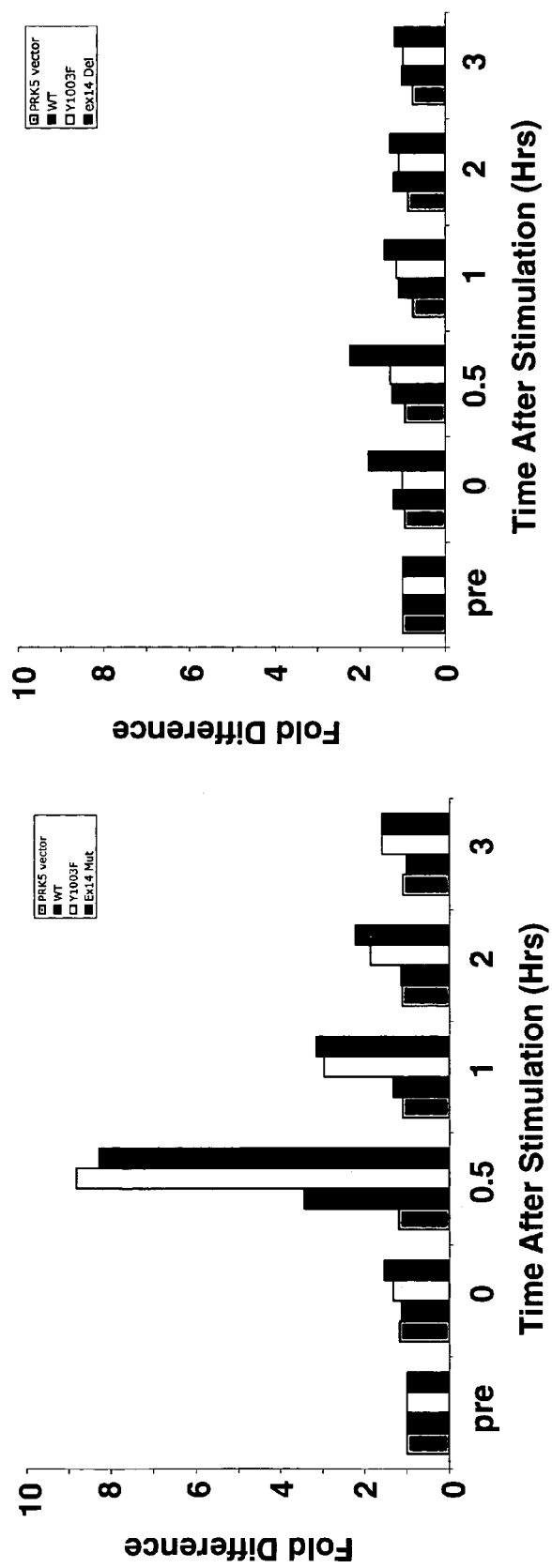
FIG._5

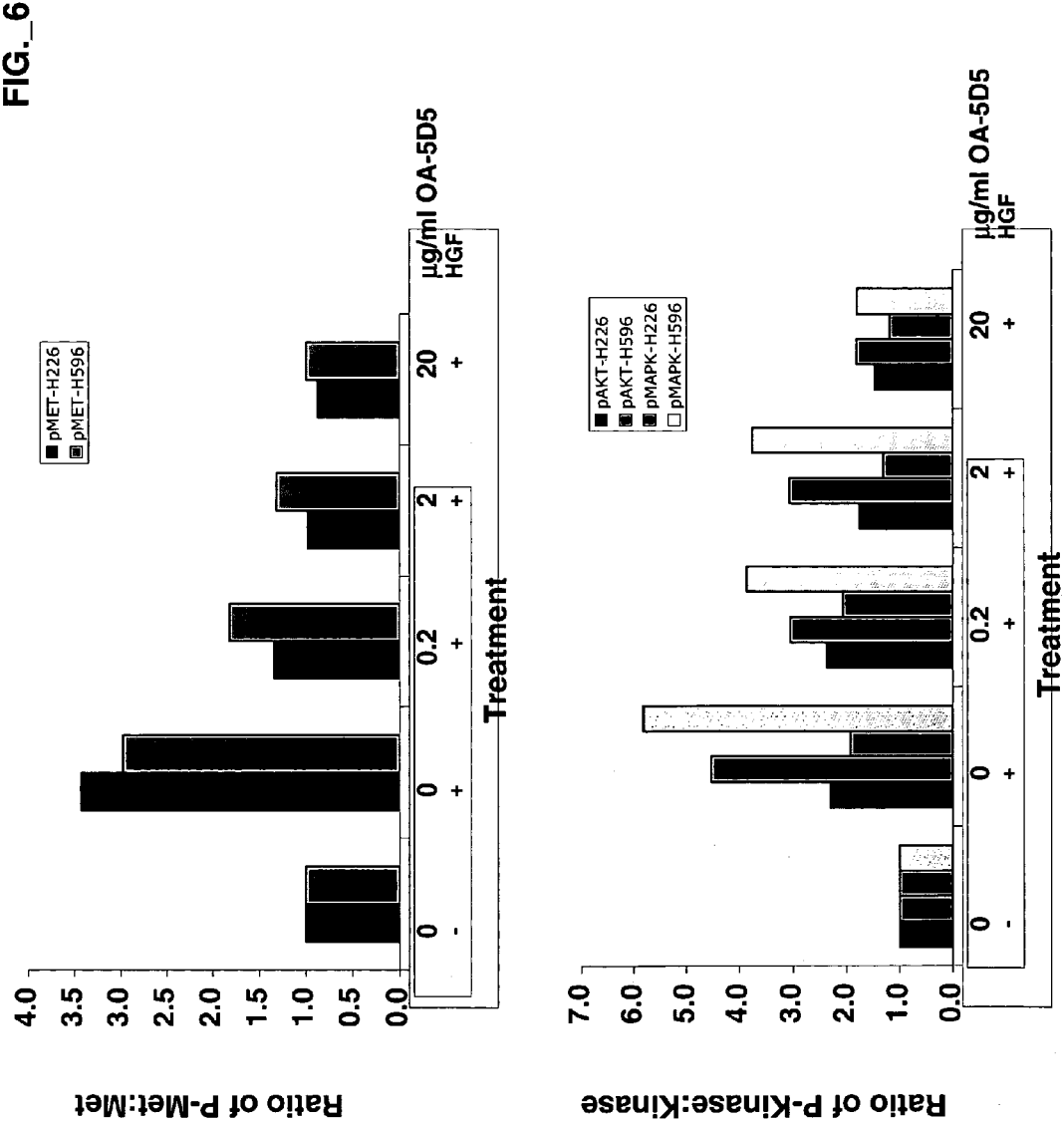
FIG._6

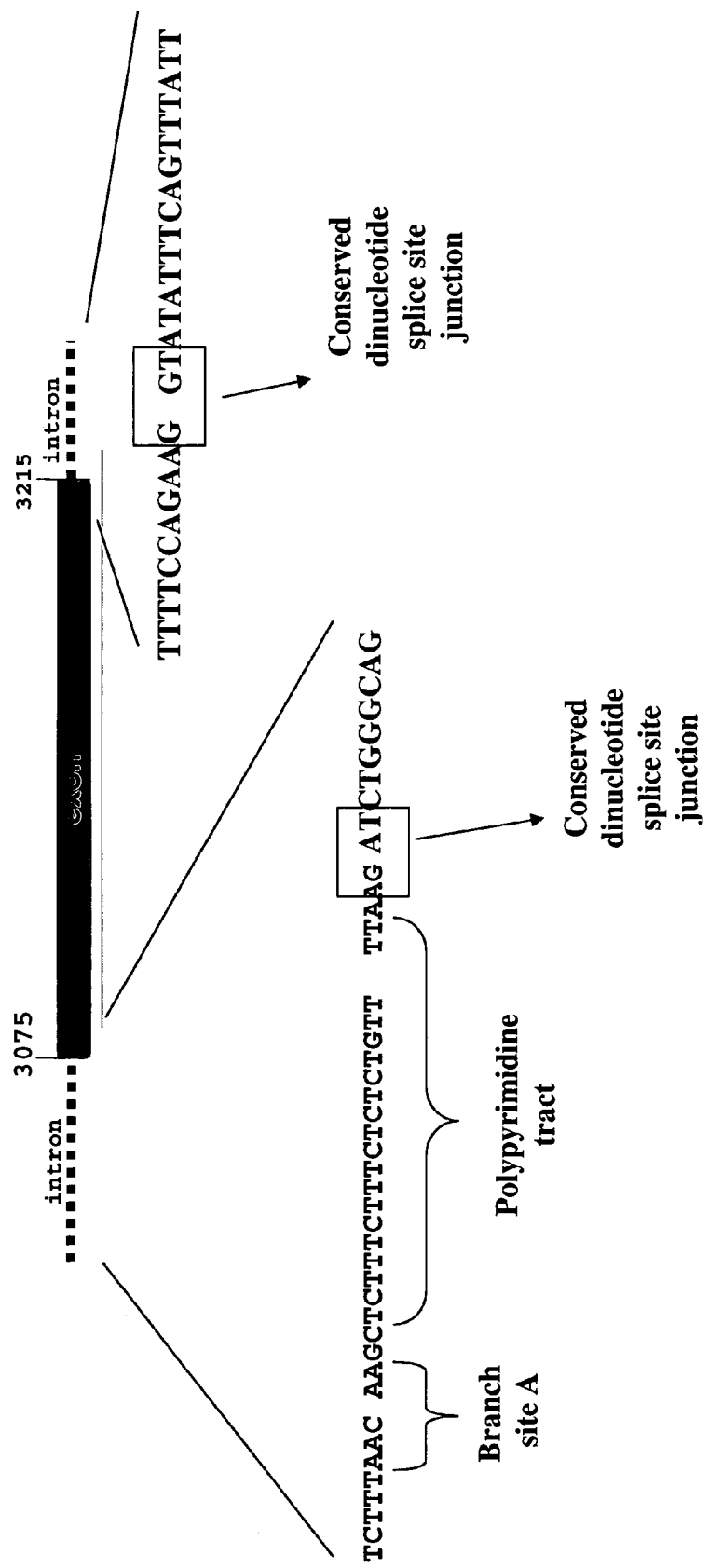
FIG._7
Illustrative splicing structures encompassing the intron/exon boundaries of human c-met exon 14

FIG. 8

```
   1  MKAPAVLAPGILVLLFTLVQRSNGECKEALAKSEMNVNMKYQLPNFTAET
  51  PIQNVILHEHHIFLGATNYIYVLNEEDLQKVAEYKTGPVLEHPDCFPCQD
 101  CSSKANLSGGVWKDNINMALVVDTYYDDQLISCGSVNRGTCQRHVFPHNH
 151  TADIQSEVHCIFSPQIEEPSQCPDCVVSALGAKVLSSVKDRFINFFVGNT
 201  INSSYFPDHPLHSISVRRLKETKDGFMFLTDQSYIDVLPEFRDSYPIKYV
 251  HAFESNNFIYFLTVQRETLDAQTFHTRIIRFCSINSGLHSYMEMPLECIL
 301  TEKRKKRSTKKEVFNILQAAYVSKPGAQLARQIGASLNDDILFGVFAQSK
 351  PDSAEPMDRSAMCAFPIKYVNDFFNKIVNKNNVRCLQHFYGPNHEHCFNR
 401  TLLRNSSGCEARRDEYRTEFTTALQRVDLFMGQFSEVLLTSISTFIKGDL
 451  TIANLGTSEGRFMQVVVSRSGPSTPHVNFLLDSHPVSPEVIVEHTLNQNG
 501  YTLVITGKKITKIPLNGLGCRHFQSCSQCLSAPPFVQCGWCHDKCVRSEE
 551  CLSGTWTQQICLPAIYKVFPNSAPLEGGTRLTICGWDFGFRRNNKFDLKK
 601  TRVLLGNESCTLTLSESTMNTLKCTVGPAMNKHFNMSIIISNGHGTTQYS
 651  TFSYVDPVITSISPKYGPMAGGTLLTLTGNYLNSGNSRHISIGGKTCTLK
 701  SVSNSILECYTPAQTISTEFAVKLKIDLANRETSIFSYREDPIVYEIHPT
 751  KSFISGGSTITGVGKNLNSVSVPRMVINVHEAGRNFTVACQHRSNSEIIC
 801  CTTPSLQQLNLQLPLKTKAFFMLDGILSKYFDLIYVHNPVFKPFEKPVMI
 851  SMGNENVLEIKGNDIDPEAVKGEVLKVGNKSCENIHLHSEAVLCTVPNDL
 901  LKLNSELNIEWKQAISSTVLGKVIVQPDQNFTGLIAGVVSISTALLLLG
 951  FFLWLKKRKQIKDLGSELVRYDARVHTPHLDRLVSARSVSPTTEMVSNES
1001  VDYRATFPEDQFPNSSQNGSCRQVQYPLTDMSPILTSGDSDISSPLLQNT
1051  VHIDLSALNPELVQAVQHVVIGPSSLIVHFNEVIGRGHFGCVYHGTLLDN
1101  DGKKIHCAVKSLNRITDIGEVSQFLTEGIIMKDFSHPNVLSLLGICLRSE
1151  GSPLVVLPYMKHGDLRNFIRNETHNPTVKDLIGFGLQVAKAMKYLASKKF
1201  VHRDLAARNCMLDEKFTVKVADFGLARDMYDKEYYSVHNKTGAKLPVKWM
1251  ALESLQTQKFTTKSDVWSFGVVLWELMTRGAPPYPDVNTFDITVYLLQGR
1301  RLLQPEYCPDPLYEVMLKCWHPKAEMRPSFSELVSRISAIFSTFIGEHYV
1351  HVNATYVNVKCVAPYPSLLSSEDNADDEVDTRPASFWETS (SEQ ID NO: ___)
```

FIG. 9

Light chain variable domain sequence of anti-c-met OA-5D5

DIQMTQSPSSLSASVGDRVTITCKSSQSLLYTSSQKNYLAWYQQKPGKAPKLLIYWASTRESGVPSRFSGSGSGTDFTLTISSLQPEDFATYYCQQYYAYPWTFGQGTKVEIK

Heavy chain variable domain sequence of anti-c-met OA-5D5

EVQLVESGGGLVQPGGSLRLSCAASGYTFTSYWLHWVRQAPGKGLEWVGMIDPSNSDTRFNPNFKDRFTISADTSKNTAYLQMNSLRAEDTAVYYCATYRSYVTPLDYWGQGTLVTVSS

```
                        SEQUENCE LISTING

<160> NUMBER OF SEQ ID NOS: 19

<210> SEQ ID NO 1
<211> LENGTH: 5
<212> TYPE: PRT
<213> ORGANISM: Artificial sequence
<220> FEATURE:
<223> OTHER INFORMATION: Sequence is synthesized

<400> SEQUENCE: 1

Ser Tyr Trp Leu His
                5

<210> SEQ ID NO 2
<211> LENGTH: 17
<212> TYPE: PRT
<213> ORGANISM: Artificial sequence
<220> FEATURE:
<223> OTHER INFORMATION: Sequence is synthesized

<400> SEQUENCE: 2

Met Ile Asp Pro Ser Asn Ser Asp Thr Arg Phe Asn Pro Asn Phe
 1               5                  10                  15

Lys Asp

<210> SEQ ID NO 3
<211> LENGTH: 10
<212> TYPE: PRT
<213> ORGANISM: Artificial sequence
<220> FEATURE:
<223> OTHER INFORMATION: Sequence is synthesized
```

```
<400> SEQUENCE: 3

Tyr Gly Ser Tyr Val Ser Pro Leu Asp Tyr
                5                   10

<210> SEQ ID NO 4
<211> LENGTH: 17
<212> TYPE: PRT
<213> ORGANISM: Artificial sequence
<220> FEATURE:
<223> OTHER INFORMATION: Sequence is synthesized

<400> SEQUENCE: 4

Lys Ser Ser Gln Ser Leu Leu Tyr Thr Ser Ser Gln Lys Asn Tyr
  1               5                  10                  15

Leu Ala

<210> SEQ ID NO 5
<211> LENGTH: 7
<212> TYPE: PRT
<213> ORGANISM: Artificial sequence
<220> FEATURE:
<223> OTHER INFORMATION: Sequence is synthesized

<400> SEQUENCE: 5

Trp Ala Ser Thr Arg Glu Ser
                5

<210> SEQ ID NO 6
<211> LENGTH: 9
<212> TYPE: PRT
<213> ORGANISM: Artificial sequence
<220> FEATURE:
<223> OTHER INFORMATION: Sequence is synthesized

<400> SEQUENCE: 6

Gln Gln Tyr Tyr Ala Tyr Pro Trp Thr
                5

<210> SEQ ID NO 7
<211> LENGTH: 119
<212> TYPE: PRT
<213> ORGANISM: Artificial sequence
<220> FEATURE:
<223> OTHER INFORMATION: Sequence is synthesized

<400> SEQUENCE: 7

Gln Val Gln Leu Gln Gln Ser Gly Pro Glu Leu Val Arg Pro Gly
  1               5                  10                  15

Ala Ser Val Lys Met Ser Cys Arg Ala Ser Gly Tyr Thr Phe Thr
                 20                  25                  30

Ser Tyr Trp Leu His Trp Val Lys Gln Arg Pro Gly Gln Gly Leu
                 35                  40                  45

Glu Trp Ile Gly Met Ile Asp Pro Ser Asn Ser Asp Thr Arg Phe
                 50                  55                  60

Asn Pro Asn Phe Lys Asp Lys Ala Thr Leu Asn Val Asp Arg Ser
                 65                  70                  75

Ser Asn Thr Ala Tyr Met Leu Leu Ser Ser Leu Thr Ser Ala Asp
                 80                  85                  90

Ser Ala Val Tyr Tyr Cys Ala Thr Tyr Gly Ser Tyr Val Ser Pro
                 95                 100                 105

Leu Asp Tyr Trp Gly Gln Gly Thr Ser Val Thr Val Ser Ser
                110                 115
```

<210> SEQ ID NO 8
<211> LENGTH: 113
<212> TYPE: PRT
<213> ORGANISM: Artificial sequence
<220> FEATURE:
<223> OTHER INFORMATION: Sequence is synthesized

<400> SEQUENCE: 8

Asp Ile Met Met Ser Gln Ser Pro Ser Ser Leu Thr Val Ser Val
 1               5                  10                  15

Gly Glu Lys Val Thr Val Ser Cys Lys Ser Gln Ser Leu Leu
                20                  25                  30

Tyr Thr Ser Ser Gln Lys Asn Tyr Leu Ala Trp Tyr Gln Gln Lys
                35                  40                  45

Pro Gly Gln Ser Pro Lys Leu Leu Ile Tyr Trp Ala Ser Thr Arg
                50                  55                  60

Glu Ser Gly Val Pro Asp Arg Phe Thr Gly Ser Gly Ser Gly Thr
                65                  70                  75

Asp Phe Thr Leu Thr Ile Thr Ser Val Lys Ala Asp Asp Leu Ala
                80                  85                  90

Val Tyr Tyr Cys Gln Gln Tyr Tyr Ala Tyr Pro Trp Thr Phe Gly
                95                  100                 105

Gly Gly Thr Lys Leu Glu Ile Lys
                110

<210> SEQ ID NO 9
<211> LENGTH: 45
<212> TYPE: DNA
<213> ORGANISM: Homo sapiens

<400> SEQUENCE: 9
gtagactacc gagctacttt tccagaaggt atatttcagt ttatt            45

<210> SEQ ID NO 10
<211> LENGTH: 45
<212> TYPE: DNA
<213> ORGANISM: Homo sapiens

<400> SEQUENCE: 10
gtagactacc gagctacttt tccagaagtt atatttcagt ttatt            45

<210> SEQ ID NO 11
<211> LENGTH: 45
<212> TYPE: DNA
<213> ORGANISM: Homo sapiens

<400> SEQUENCE: 11
tctttaacaa gctctttctt tctctctgtt ttaagatctg ggcag            45

<210> SEQ ID NO 12
<211> LENGTH: 23
<212> TYPE: DNA
<213> ORGANISM: Homo sapiens

<400> SEQUENCE: 12
tctttaactt aagatctggg cag                                    23

<210> SEQ ID NO 13
<211> LENGTH: 45
<212> TYPE: DNA

-continued

<213> ORGANISM: Homo sapiens

<400> SEQUENCE: 13
gtagactacc gagctacttt tccagaaggt atatttcagt ttatt                45

<210> SEQ ID NO 14
<211> LENGTH: 17
<212> TYPE: DNA
<213> ORGANISM: Homo sapiens

<400> SEQUENCE: 14
gtagacttca gtttatt                                               17

<210> SEQ ID NO 15
<211> LENGTH: 28
<212> TYPE: DNA
<213> ORGANISM: Homo sapiens

<400> SEQUENCE: 15
ttttccagaa ggtatatttc agtttatt                                   28

<210> SEQ ID NO 16
<211> LENGTH: 45
<212> TYPE: DNA
<213> ORGANISM: Homo sapiens

<400> SEQUENCE: 16
tctttaacaa gctctttctt tctctctgtt ttaagatctg ggcag                45

<210> SEQ ID NO 17
<211> LENGTH: 1390
<212> TYPE: PRT
<213> ORGANISM: Homo sapiens

<400> SEQUENCE: 17

Met Lys Ala Pro Ala Val Leu Ala Pro Gly Ile Leu Val Leu Leu
 1               5                  10                  15

Phe Thr Leu Val Gln Arg Ser Asn Gly Glu Cys Lys Glu Ala Leu
                20                  25                  30

Ala Lys Ser Glu Met Asn Val Asn Met Lys Tyr Gln Leu Pro Asn
                35                  40                  45

Phe Thr Ala Glu Thr Pro Ile Gln Asn Val Ile Leu His Glu His
                50                  55                  60

His Ile Phe Leu Gly Ala Thr Asn Tyr Ile Tyr Val Leu Asn Glu
                65                  70                  75

Glu Asp Leu Gln Lys Val Ala Glu Tyr Lys Thr Gly Pro Val Leu
                80                  85                  90

Glu His Pro Asp Cys Phe Pro Cys Gln Asp Cys Ser Ser Lys Ala
                95                  100                 105

Asn Leu Ser Gly Gly Val Trp Lys Asp Asn Ile Asn Met Ala Leu
                110                 115                 120

Val Val Asp Thr Tyr Tyr Asp Asp Gln Leu Ile Ser Cys Gly Ser
                125                 130                 135

Val Asn Arg Gly Thr Cys Gln Arg His Val Phe Pro His Asn His
                140                 145                 150

Thr Ala Asp Ile Gln Ser Glu Val His Cys Ile Phe Ser Pro Gln
                155                 160                 165

Ile Glu Glu Pro Ser Gln Cys Pro Asp Cys Val Val Ser Ala Leu
                170                 175                 180

-continued

```
Gly Ala Lys Val Leu Ser Ser Val Lys Asp Arg Phe Ile Asn Phe
            185                 190                 195
Phe Val Gly Asn Thr Ile Asn Ser Ser Tyr Phe Pro Asp His Pro
            200                 205                 210
Leu His Ser Ile Ser Val Arg Arg Leu Lys Glu Thr Lys Asp Gly
            215                 220                 225
Phe Met Phe Leu Thr Asp Gln Ser Tyr Ile Asp Val Leu Pro Glu
            230                 235                 240
Phe Arg Asp Ser Tyr Pro Ile Lys Tyr Val His Ala Phe Glu Ser
            245                 250                 255
Asn Asn Phe Ile Tyr Phe Leu Thr Val Gln Arg Glu Thr Leu Asp
            260                 265                 270
Ala Gln Thr Phe His Thr Arg Ile Ile Arg Phe Cys Ser Ile Asn
            275                 280                 285
Ser Gly Leu His Ser Tyr Met Glu Met Pro Leu Glu Cys Ile Leu
            290                 295                 300
Thr Glu Lys Arg Lys Lys Arg Ser Thr Lys Lys Glu Val Phe Asn
            305                 310                 315
Ile Leu Gln Ala Ala Tyr Val Ser Lys Pro Gly Ala Gln Leu Ala
            320                 325                 330
Arg Gln Ile Gly Ala Ser Leu Asn Asp Asp Ile Leu Phe Gly Val
            335                 340                 345
Phe Ala Gln Ser Lys Pro Asp Ser Ala Glu Pro Met Asp Arg Ser
            350                 355                 360
Ala Met Cys Ala Phe Pro Ile Lys Tyr Val Asn Asp Phe Phe Asn
            365                 370                 375
Lys Ile Val Asn Lys Asn Asn Val Arg Cys Leu Gln His Phe Tyr
            380                 385                 390
Gly Pro Asn His Glu His Cys Phe Asn Arg Thr Leu Leu Arg Asn
            395                 400                 405
Ser Ser Gly Cys Glu Ala Arg Arg Asp Glu Tyr Arg Thr Glu Phe
            410                 415                 420
Thr Thr Ala Leu Gln Arg Val Asp Leu Phe Met Gly Gln Phe Ser
            425                 430                 435
Glu Val Leu Leu Thr Ser Ile Ser Thr Phe Ile Lys Gly Asp Leu
            440                 445                 450
Thr Ile Ala Asn Leu Gly Thr Ser Glu Gly Arg Phe Met Gln Val
            455                 460                 465
Val Val Ser Arg Ser Gly Pro Ser Thr Pro His Val Asn Phe Leu
            470                 475                 480
Leu Asp Ser His Pro Val Ser Pro Glu Val Ile Val Glu His Thr
            485                 490                 495
Leu Asn Gln Asn Gly Tyr Thr Leu Val Ile Thr Gly Lys Lys Ile
            500                 505                 510
Thr Lys Ile Pro Leu Asn Gly Leu Gly Cys Arg His Phe Gln Ser
            515                 520                 525
Cys Ser Gln Cys Leu Ser Ala Pro Pro Phe Val Gln Cys Gly Trp
            530                 535                 540
Cys His Asp Lys Cys Val Arg Ser Glu Glu Cys Leu Ser Gly Thr
            545                 550                 555
Trp Thr Gln Gln Ile Cys Leu Pro Ala Ile Tyr Lys Val Phe Pro
            560                 565                 570
```

-continued

```
Asn Ser Ala Pro Leu Glu Gly Gly Thr Arg Leu Thr Ile Cys Gly
                575                 580                 585

Trp Asp Phe Gly Phe Arg Arg Asn Asn Lys Phe Asp Leu Lys Lys
                590                 595                 600

Thr Arg Val Leu Leu Gly Asn Glu Ser Cys Thr Leu Thr Leu Ser
                605                 610                 615

Glu Ser Thr Met Asn Thr Leu Lys Cys Thr Val Gly Pro Ala Met
                620                 625                 630

Asn Lys His Phe Asn Met Ser Ile Ile Ile Ser Asn Gly His Gly
                635                 640                 645

Thr Thr Gln Tyr Ser Thr Phe Ser Tyr Val Asp Pro Val Ile Thr
                650                 655                 660

Ser Ile Ser Pro Lys Tyr Gly Pro Met Ala Gly Gly Thr Leu Leu
                665                 670                 675

Thr Leu Thr Gly Asn Tyr Leu Asn Ser Gly Asn Ser Arg His Ile
                680                 685                 690

Ser Ile Gly Gly Lys Thr Cys Thr Leu Lys Ser Val Ser Asn Ser
                695                 700                 705

Ile Leu Glu Cys Tyr Thr Pro Ala Gln Thr Ile Ser Thr Glu Phe
                710                 715                 720

Ala Val Lys Leu Lys Ile Asp Leu Ala Asn Arg Glu Thr Ser Ile
                725                 730                 735

Phe Ser Tyr Arg Glu Asp Pro Ile Val Tyr Glu Ile His Pro Thr
                740                 745                 750

Lys Ser Phe Ile Ser Gly Gly Ser Thr Ile Thr Gly Val Gly Lys
                755                 760                 765

Asn Leu Asn Ser Val Ser Val Pro Arg Met Val Ile Asn Val His
                770                 775                 780

Glu Ala Gly Arg Asn Phe Thr Val Ala Cys Gln His Arg Ser Asn
                785                 790                 795

Ser Glu Ile Ile Cys Cys Thr Thr Pro Ser Leu Gln Gln Leu Asn
                800                 805                 810

Leu Gln Leu Pro Leu Lys Thr Lys Ala Phe Phe Met Leu Asp Gly
                815                 820                 825

Ile Leu Ser Lys Tyr Phe Asp Leu Ile Tyr Val His Asn Pro Val
                830                 835                 840

Phe Lys Pro Phe Glu Lys Pro Val Met Ile Ser Met Gly Asn Glu
                845                 850                 855

Asn Val Leu Glu Ile Lys Gly Asn Asp Ile Asp Pro Glu Ala Val
                860                 865                 870

Lys Gly Glu Val Leu Lys Val Gly Asn Lys Ser Cys Glu Asn Ile
                875                 880                 885

His Leu His Ser Glu Ala Val Leu Cys Thr Val Pro Asn Asp Leu
                890                 895                 900

Leu Lys Leu Asn Ser Glu Leu Asn Ile Glu Trp Lys Gln Ala Ile
                905                 910                 915

Ser Ser Thr Val Leu Gly Lys Val Ile Val Gln Pro Asp Gln Asn
                920                 925                 930

Phe Thr Gly Leu Ile Ala Gly Val Val Ser Ile Ser Thr Ala Leu
                935                 940                 945

Leu Leu Leu Leu Gly Phe Phe Leu Trp Leu Lys Lys Arg Lys Gln
                950                 955                 960

Ile Lys Asp Leu Gly Ser Glu Leu Val Arg Tyr Asp Ala Arg Val
```

-continued

```
                965                 970                 975
His Thr Pro His Leu Asp Arg Leu Val Ser Ala Arg Ser Val Ser
                980                 985                 990

Pro Thr Thr Glu Met Val Ser Asn Glu Ser Val Asp Tyr Arg Ala
                995                1000                1005

Thr Phe Pro Glu Asp Gln Phe Pro Asn Ser Ser Gln Asn Gly Ser
               1010                1015                1020

Cys Arg Gln Val Gln Tyr Pro Leu Thr Asp Met Ser Pro Ile Leu
               1025                1030                1035

Thr Ser Gly Asp Ser Asp Ile Ser Ser Pro Leu Leu Gln Asn Thr
               1040                1045                1050

Val His Ile Asp Leu Ser Ala Leu Asn Pro Glu Leu Val Gln Ala
               1055                1060                1065

Val Gln His Val Val Ile Gly Pro Ser Ser Leu Ile Val His Phe
               1070                1075                1080

Asn Glu Val Ile Gly Arg Gly His Phe Gly Cys Val Tyr His Gly
               1085                1090                1095

Thr Leu Leu Asp Asn Asp Gly Lys Lys Ile His Cys Ala Val Lys
               1100                1105                1110

Ser Leu Asn Arg Ile Thr Asp Ile Gly Glu Val Ser Gln Phe Leu
               1115                1120                1125

Thr Glu Gly Ile Ile Met Lys Asp Phe Ser His Pro Asn Val Leu
               1130                1135                1140

Ser Leu Leu Gly Ile Cys Leu Arg Ser Glu Gly Ser Pro Leu Val
               1145                1150                1155

Val Leu Pro Tyr Met Lys His Gly Asp Leu Arg Asn Phe Ile Arg
               1160                1165                1170

Asn Glu Thr His Asn Pro Thr Val Lys Asp Leu Ile Gly Phe Gly
               1175                1180                1185

Leu Gln Val Ala Lys Ala Met Lys Tyr Leu Ala Ser Lys Lys Phe
               1190                1195                1200

Val His Arg Asp Leu Ala Ala Arg Asn Cys Met Leu Asp Glu Lys
               1205                1210                1215

Phe Thr Val Lys Val Ala Asp Phe Gly Leu Ala Arg Asp Met Tyr
               1220                1225                1230

Asp Lys Glu Tyr Tyr Ser Val His Asn Lys Thr Gly Ala Lys Leu
               1235                1240                1245

Pro Val Lys Trp Met Ala Leu Glu Ser Leu Gln Thr Gln Lys Phe
               1250                1255                1260

Thr Thr Lys Ser Asp Val Trp Ser Phe Gly Val Val Leu Trp Glu
               1265                1270                1275

Leu Met Thr Arg Gly Ala Pro Pro Tyr Pro Asp Val Asn Thr Phe
               1280                1285                1290

Asp Ile Thr Val Tyr Leu Leu Gln Gly Arg Arg Leu Leu Gln Pro
               1295                1300                1305

Glu Tyr Cys Pro Asp Pro Leu Tyr Glu Val Met Leu Lys Cys Trp
               1310                1315                1320

His Pro Lys Ala Glu Met Arg Pro Ser Phe Ser Glu Leu Val Ser
               1325                1330                1335

Arg Ile Ser Ala Ile Phe Ser Thr Phe Ile Gly Glu His Tyr Val
               1340                1345                1350

His Val Asn Ala Thr Tyr Val Asn Val Lys Cys Val Ala Pro Tyr
               1355                1360                1365
```

Pro Ser Leu Leu Ser Ser Glu Asp Asn Ala Asp Asp Glu Val Asp
            1370                1375                1380

Thr Arg Pro Ala Ser Phe Trp Glu Thr Ser
            1385                1390

<210> SEQ ID NO 18
<211> LENGTH: 113
<212> TYPE: PRT
<213> ORGANISM: Artificial sequence
<220> FEATURE:
<223> OTHER INFORMATION: Sequence is synthesized

<400> SEQUENCE: 18

Asp Ile Gln Met Thr Gln Ser Pro Ser Ser Leu Ser Ala Ser Val
  1               5                  10                  15

Gly Asp Arg Val Thr Ile Thr Cys Lys Ser Ser Gln Ser Leu Leu
                 20                  25                  30

Tyr Thr Ser Ser Gln Lys Asn Tyr Leu Ala Trp Tyr Gln Gln Lys
                 35                  40                  45

Pro Gly Lys Ala Pro Lys Leu Leu Ile Tyr Trp Ala Ser Thr Arg
                 50                  55                  60

Glu Ser Gly Val Pro Ser Arg Phe Ser Gly Ser Gly Ser Gly Thr
                 65                  70                  75

Asp Phe Thr Leu Thr Ile Ser Ser Leu Gln Pro Glu Asp Phe Ala
                 80                  85                  90

Thr Tyr Tyr Cys Gln Gln Tyr Tyr Ala Tyr Pro Trp Thr Phe Gly
                 95                 100                 105

Gln Gly Thr Lys Val Glu Ile Lys
                110

<210> SEQ ID NO 19
<211> LENGTH: 119
<212> TYPE: PRT
<213> ORGANISM: Artificial sequence
<220> FEATURE:
<223> OTHER INFORMATION: Sequence is synthesized

<400> SEQUENCE: 19

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
                 20                  25                  30

Ser Tyr Trp Leu His Trp Val Arg Gln Ala Pro Gly Lys Gly Leu
                 35                  40                  45

Glu Trp Val Gly Met Ile Asp Pro Ser Asn Ser Asp Thr Arg Phe
                 50                  55                  60

Asn Pro Asn Phe Lys Asp Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Thr Tyr Arg Ser Tyr Val Thr Pro
                 95                 100                 105

Leu Asp Tyr Trp Gly Gln Gly Thr Leu Val Thr Val Ser Ser
                110                 115

METHODS AND COMPOSITIONS FOR MODULATING HYPERSTABILIZED C-MET

RELATED APPLICATIONS

This application is a non-provisional application filed under 37 CFR 1.53(b)(1), claiming priority under 35 USC 119(e) to provisional application No. 60/665,482 filed Mar. 25, 2005, the contents of which are incorporated herein by reference.

TECHNICAL FIELD

The present invention relates generally to the fields of molecular biology and growth factor regulation. More specifically, the invention concerns modulators of the HGF/c-met signaling pathway, and uses of said modulators.

BACKGROUND

HGF is a mesenchyme-derived pleiotrophic factor with mitogenic, motogenic and morphogenic activities on a number of different cell types. HGF effects are mediated through a specific tyrosine kinase, c-met, and aberrant HGF and c-met expression are frequently observed in a variety of tumors. See, e.g., Maulik et al., Cytokine & Growth Factor Reviews (2002), 13:41-59; Danilkovitch-Miagkova & Zbar, J. Clin. Invest. (2002), 109(7):863-867. Regulation of the HGF/c-Met signaling pathway is implicated in tumor progression and metastasis. See, e.g., Trusolino & Comoglio, Nature Rev. (2002), 2:289-300).

HGF binds the extracellular domain of the Met receptor tyrosine kinase (RTK) and regulates diverse biological processes such as cell scattering, proliferation, and survival. HGF-Met signaling is essential for normal embryonic development especially in migration of muscle progenitor cells and development of the liver and nervous system (Bladt et al., Nature (1995), 376, 768-771.; Hamanoue et al., Faseb J (2000), 14, 399-406; Maina et al., Cell (1996), 87, 531-542; Schmidt et al., Nature (1995), 373, 699-702; Uehara et al., Nature (1995), 373, 702-705). Developmental phenotypes of Met and HGF knockout mice are very similar suggesting that HGF is the cognate ligand for the Met receptor (Schmidt et al., 1995, supra; Uehara et al., 1995, supra). HGF-Met also plays a role in liver regeneration, angiogenesis, and wound healing (Bussolino et al., J Cell Biol (1992), 119, 629-641; Matsumoto and Nakamura, Exs (1993), 65, 225-249; Nusrat et al., J Clin Invest (1994) 93, 2056-2065). The precursor Met receptor undergoes proteolytic cleavage into an extracellular α subunit and membrane spanning β subunit linked by disulfide bonds (Tempest et al., Br J Cancer (1988), 58, 3-7). The β subunit contains the cytoplasmic kinase domain and harbors a multi-substrate docking site at the C-terminus where adapter proteins bind and initiate signaling (Bardelli et al., Oncogene (1997), 15, 3103-3111; Nguyen et al., J Biol Chem (1997), 272, 20811-20819; Pelicci et al., Oncogene (1995), 10, 1631-1638; Ponzetto et al., Cell (1994), 77, 261-271; Weidner et al., Nature (1996), 384, 173-176). Upon HGF binding, activation of Met leads to tyrosine phosphorylation and downstream signaling through Gab1 and Grb2/Sos mediated PI3-kinase and Ras/MAPK activation respectively, which drives cell motility and proliferation (Furge et al., Oncogene (2000), 19, 5582-5589; Hartmann et al., J Biol Chem (1994), 269, 21936-21939; Ponzetto et al., J Biol Chem (1996), 271, 14119-14123; Royal and Park, J Biol Chem (1995), 276, 27780-27787).

Met was shown to be transforming in a carcinogen-treated osteosarcoma cell line (Cooper et al., Nature (1984), 311, 29-33; Park et al., Cell (1986), 45, 895-904). Met overexpression or gene-amplification has been observed in a variety of human cancers. For example, Met protein is overexpressed at least 5-fold in colorectal cancers and reported to be gene-amplified in liver metastasis (Di Renzo et al., Clin Cancer Res (1995), 1, 147-154; Liu et al., Oncogene (1992), 7, 181-185). Met protein is also reported to be overexpressed in oral squamous cell carcinoma, hepatocellular carcinoma, renal cell carcinoma, breast carcinoma, and lung carcinoma (Jin et al., Cancer (1997), 79, 749-760; Morello et al., J Cell Physiol (2001), 189, 285-290; Natali et al., Int J Cancer (1996), 69, 212-217; Olivero et al., Br J Cancer (1996), 74, 1862-1868; Suzuki et al., Br J Cancer (1996), 74, 1862-1868). In addition, overexpression of mRNA has been observed in hepatocellular carcinoma, gastric carcinoma, and colorectal carcinoma (Boix et al., Hepatology (1994), 19, 88-91; Kuniyasu et al., Int J Cancer (1993), 55, 72-75; Liu et al., Oncogene (1992), 7, 181-185).

A number of mutations in the kinase domain of Met have been found in renal papillary carcinoma which leads to constitutive receptor activation (Olivero et al., Int J Cancer (1999), 82, 640-643; Schmidt et al., Nat Genet (1997), 16, 68-73; Schmidt et al., Oncogene (1999), 18, 2343-2350). These activating mutations confer constitutive Met tyrosine phosphorylation and result in MAPK activation, focus formation, and tumorigenesis (Jeffers et al., Proc Natl Acad Sci USA (1997), 94, 11445-11450). In addition, these mutations enhance cell motility and invasion (Giordano et al., Faseb J (2000), 14, 399-406; Lorenzato et al., Cancer Res (2002), 62, 7025-7030). HGF-dependent Met activation in transformed cells mediates increased motility, scattering, and migration which eventually leads to invasive tumor growth and metastasis (Jeffers et al., Mol Cell Biol (1996), 16, 1115-1125; Meiners et al., Oncogene (1998), 16, 9-20).

Met has been shown to interact with other proteins that drive receptor activation, transformation, and invasion. In neoplastic cells, Met is reported to interact with α6β4 integrin, a receptor for extracellular matrix (ECM) components such as laminins, to promote HGF-dependent invasive growth (Trusolino et al., Cell (2001), 107, 643-654). In addition, the extracellular domain of Met has been shown to interact with a member of the semaphorin family, plexin B1, and to enhance invasive growth (Giordano et al., Nat Cell Biol (2002), 4, 720-724). Furthermore, CD44v6, which has been implicated in tumorigenesis and metastasis, is also reported to form a complex with Met and HGF and result in Met receptor activation (Orian-Rousseau et al., Genes Dev (2002), 16, 3074-3086).

Met is a member of the subfamily of receptor tyrosine kinases (RTKs) which include Ron and Sea (Maulik et al., Cytokine Growth Factor Rev (2002), 13, 41-59). Prediction of the extracellular domain structure of Met suggests shared homology with the semaphorins and plexins. The N-terminus of Met contains a Sema domain of approximately 500 amino acids that is conserved in all semaphorins and plexins. The semaphorins and plexins belong to a large family of secreted and membrane-bound proteins first described for their role in neural development (Van Vactor and Lorenz, Curr Bio (1999), 19, R201-204). However, more recently semaphorin overexpression has been correlated with tumor invasion and metastasis. A cysteine-rich PSI domain (also referred to as a Met Related Sequence domain) found in plexins, semaphorins, and integrins lies adjacent to the Sema domain followed by four IPT repeats that are immunoglobulin-like regions found in plexins and transcription factors. A recent study suggests that the Met Sema domain is sufficient for HGF and heparin binding (Gherardi et al., Proc Natl Acad Sci USA (2003), 100(21):12039-44).

As noted above, the Met receptor tyrosine kinase is activated by its cognate ligand HGF and receptor phosphorylation activates downstream pathways of MAPK, PI-3 kinase and PLC-γ (1, 2). Phosphorylation of Y1234/Y1235 within the kinase domain is critical for Met kinase activation while Y1349 and Y1356 in the multisubstrate docking site are important for binding of src homology-2 (SH2), phosphotyrosine binding (PTB), and Met binding domain (MBD) proteins (3-5), to mediate activation of downstream signaling pathways. An additional juxtamembrane phosphorylation site, Y1003, has been well characterized for its binding to the tyrosine kinase binding (TKB) domain of the Cbl E3-ligase (6, 7). Cbl binding is reported to drive endophilin-mediated receptor endocytosis, ubiquitination, and subsequent receptor degradation (8). This mechanism of receptor downregulation has been described previously in the EGFR family that also harbor a similar Cbl binding site (9-11).

Dysregulation of Met and HGF have been reported in a variety of tumors. Ligand-driven Met activation has been observed in several cancers. Elevated serum and intra-tumoral HGF is observed in lung, breast cancer, and multiple myeloma (12-15). Overexpression of Met and/or HGF, Met amplification or mutation has been reported in various cancers such as colorectal, lung, gastric, and kidney cancer and is thought to drive ligand-independent receptor activation (2, 16). Additionally, inducible overexpression of Met in a liver mouse model gives rise to hepatocellular carcinoma demonstrating that receptor overexpression drives ligand independent tumorigenesis (17). The most compelling evidence implicating Met in cancer is reported in familial and sporadic renal papillary carcinoma (RPC) patients. Mutations in the kinase domain of Met that lead to constitutive activation of the receptor were identified as germline and somatic mutations in RPC (18). Introduction of these mutations in transgenic mouse models leads to tumorigenesis and metastasis. (19).

Although the role of the Met kinase domain has been investigated in detail, and it has been theorized that increased expression levels of HGF/c-met probably underlie development of some cancers, direct evidence for a biological role for non-kinase domains of c-met has been lacking. Indeed, despite being implicated in the etiology of a variety of oncological conditions, the HGF/-c-met pathway has been a difficult pathway to target therapeutically. Efforts in this regard have been impeded in large part by a lack of understanding regarding mechanisms of action by which dysregulation of HGF/c-met causes tumorigenesis. Therefore, it is clear that the need for greater understanding of c-met-related oncogenic mechanisms of action is great. The invention provided herein meets this need and provides other benefits.

All references cited herein, including patent applications and publications, are incorporated by reference in their entirety.

DISCLOSURE OF THE INVENTION

The invention is based at least in part on the novel finding that certain human tumors express a mutated c-met protein that exhibits decreased rates of down-regulation intracellularly, yet are capable of cell signaling. These "hyperstabilized" c-met proteins were found to have increased oncogenic activity compared to wild-type c-met. As shown herein, these tumors can be inhibited by anti-c-met inhibitors. Inhibition of hyperstabilized c-met activity provides numerous therapeutic advantages. For example, since these c-met mutants are particularly oncogenic, their targeted inhibition would be expected to diminish tumorigenesis driven by these mutants. Moreover, since c-met is found in many cell types, including normal cells, the ability to specifically target tumor-specific c-met mutants would be particularly beneficial, for example in reducing side-effects of c-met inhibition therapy. The invention provides methods and compositions based on the findings described herein, and are useful for targeting and/or treating tumors having hyperstabilized c-met.

In one aspect, the invention provides a substance capable of specifically binding to hyperstabilized c-met. In one embodiment, the substance comprises an inhibitory activity against biological activity associated with the hyperstabilized c-met. In another embodiment, the substance is capable of specific binding to the hyperstabilized c-met. In one embodiment, the substance binds to hyperstabilized c-met and inhibits c-met activity. In one embodiment, the substance binds to hyperstabilized c-met without substantially inhibiting c-met activity. These substances find a variety of uses, for example as molecules for targeting therapeutic agents to a cell expressing hyperstabilized c-met. Therapeutic agents include any of the agents described herein, e.g. toxins. Substances can be in any suitable form, including in the form of antibody-drug conjugations and fusion polypeptides.

In one aspect, the invention provides c-met antagonists that disrupt HGF/c-met signaling associated with a hyperstabilized c-met protein. In one embodiment, the invention provides an antagonist that inhibits c-met signaling activity of a human hyperstabilized c-met polypeptide, wherein the hyperstabilized c-met polypeptide comprises a deletion of at least a portion of exon 14 such that its rate of degradation in a cell is diminished compared to wild type c-met, and wherein the hyperstabilized c-met polypeptide has c-met signaling activity.

An antagonist of the invention can be of any form capable of specifically inhibiting activity of a hyperstabilized c-met molecule as described herein. In one embodiment, an antagonist of the invention comprises an antibody. In one embodiment, an antibody of the invention specifically binds to an epitope formed by in-frame splicing of exon 13 and exon 15 of c-met. In one embodiment, at least a portion of exon 14 is deleted as a result of said in-frame splicing. In another aspect, an antagonist of the invention comprises an aptamer. In one embodiment, an aptamer of the invention specifically binds to an epitope formed by in-frame splicing of exon 13 and exon 15 of c-met. In one embodiment, at least a portion of exon 14 is deleted as a result of said in-frame splicing. In one aspect, an antagonist of the invention comprises an inhibitory RNA that preferentially/selectively inhibits expression from a nucleic acid molecule encoding a splice variant of c-met wherein exon 13 is spliced to exon 15. In one embodiment, the nucleic acid encodes a hyperstabilized c-met in which at least a portion of exon 14 is deleted as a result of variant splicing. In one aspect, the invention provides an antagonist comprising an antisense oligonucleotide that preferentially/selectively inhibits a nucleic acid molecule encoding a splice variant of c-met wherein exon 13 is spliced to exon 15. In one embodiment, the nucleic acid molecule encodes a hyperstabilized c-met in which at least a portion of exon 14 is deleted as a result of variant splicing.

Inhibition of c-met activity can be effected in any of a number of ways known in the art, so long as biological activity of hyperstabilized c-met is diminished in a cell. For example, in one embodiment, inhibition of c-met activity by an antagonist of the invention comprises enhancement of cellular degradation of the hyperstabilized c-met protein. In another embodiment, inhibition of c-met activity by an antagonist of the invention comprises inhibition of phosphorylation of the hyperstabilized c-met protein. In yet another embodiment, inhibition of c-met activity by an antagonist of the invention comprises inhibition of phosphorylation of a member of the HGF/c-met signaling pathway by the hyperstabilized c-met. Inhibition of c-met activity by an antagonist of the invention can also be effected by reduction of levels of hyperstabilized c-met polypeptide in a cell. Thus, for example, in one embodiment, inhibition of c-met activity by an antagonist of the invention comprises inhibition of expression of hyperstabilized c-met protein, for example transcription and/or translation from a polynucleotide encoding a hyperstabilized c-met polypeptide. In another embodiment, inhibition of c-met activity by an antagonist of the invention comprises cell death associatd with a cytotoxin linked to a molecule (e.g., an antibody-drug conjugate) that specifically binds to hyperstabilized c-met in a cell.

In one embodiment, an antagonist of the invention is a monoclonal antibody, antibody fragment, chimeric antibody, humanized antibody, human antibody, multi-specific antibody or single-chain antibody. Antagonists employed in the methods of the invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. In some embodiments of methods of the invention, a chemotherapeutic agent is also administered to the subject.

In general, effective c-met antagonists include c-met inhibitors that interfere with binding of a ligand such as HGF to hyperstabilized c-met. For example, a c-met inhibitor may bind to hyperstabilized c-met such that binding of HGF to c-met is inhibited. In one embodiment, an antagonist antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g. obtained by mutagenesis (e.g., phage display screening, etc.). In one embodiment, a chimeric antibody of the invention has murine V regions and human C region. In one embodiment, the murine light chain V region is fused to a human kappa light chain. In one embodiment, the murine heavy chain V region is fused to a human IgG1 C region. In one embodiment, the antigen binding sequences comprise at least one, at least two or all three CDRs of a light and/or heavy chain. In one embodiment, the antigen binding sequences comprise a heavy chain CDR3. In one embodiment, the antigen binding sequences comprise part or all of the CDR and/or variable domain sequences of the monoclonal antibody produced by the hybridoma cell line deposited under American Type Culture Collection Accession Number ATCC HB-11894 (hybridoma 1A3.3.13) or HB-11895 (hybridoma 5D5.11.6). In one embodiment, the antigen binding sequences comprise at least CDR3 of the heavy chain of the monoclonal antibody produced by the hybridoma cell line 1A3.3.13 or 5D5.11.6. Humanized antibodies of the invention include those that have amino acid substitutions in the FR and affinity maturation variants with changes in the grafted CDRs. The substituted amino acids in the CDR or FR are not limited to those present in the donor or recipient antibody. In other embodiments, the antibodies of the invention further comprise changes in amino acid residues in the Fc region that lead to improved effector function including enhanced CDC and/or ADCC function and B-cell killing. Other antibodies of the invention include those having specific changes that improve stability. Antibodies of the invention also include fucose deficient variants having improved ADCC function in vivo.

In one embodiment, an antibody fragment of the invention comprises an antigen binding arm comprising a heavy chain comprising at least one, at least two or all three of CDR sequences selected from the group consisting of SYWLH (SEQ ID NO:1), MIDPSNSDTRFNPNFKD (SEQ ID NO:2) and YGSYVSPLDY (SEQ ID NO:3). In one embodiment, the antigen binding arm comprises heavy chain CDR-H1 having amino acid sequence SYWLH. In one embodiment, the antigen binding arm comprises heavy chain CDR-H2 having amino acid sequence MIDPSNSDTRFNPNFKD. In one embodiment, the antigen binding arm comprises heavy chain CDR-H3 having amino acid sequence YGSYVSPLDY. In one embodiment, an antibody fragment of the invention comprises an antigen binding arm comprising a light chain comprising at least one, at least two or all three of CDR sequences selected from the group consisting of KSSQSLLYTSSQK-NYLA (SEQ ID NO:4), WASTRES (SEQ ID NO:5) and QQYYAYPWT (SEQ ID NO:6). In one embodiment, the antigen binding arm comprises heavy chain CDR-L1 having amino acid sequence KSSQSLLYTSSQKNYLA. In one embodiment, the antigen binding arm comprises heavy chain CDR-L2 having amino acid sequence WASTRES. In one embodiment, the antigen binding arm comprises heavy chain CDR-L3 having amino acid sequence QQYYAYPWT. In one embodiment, an antibody fragment of the invention comprises an antigen binding arm comprising a heavy chain comprising at least one, at least two or all three of CDR sequences selected from the group consisting of SYWLH (SEQ ID NO:1), MIDPSNSDTRFNPNFKD (SEQ ID NO:2) and YGSYVSPLDY (SEQ ID NO:3) and a light chain comprising at least one, at least two or all three of CDR sequences selected from the group consisting of KSSQSLLYTSSQK-NYLA (SEQ ID NO:4), WASTRES (SEQ ID NO:5) and QQYYAYPWT (SEQ ID NO:6).

The invention provides a humanized antagonist antibody that binds human hyperstabilized c-met, or an antigen-binding fragment thereof, wherein the antibody is effective to inhibit human hyperstabilized HGF/c-met activity in vivo, the antibody comprising in the H chain Variable region ($V_H$) at least a CDR3 sequence of the monoclonal antibody produced by the hybridoma cell line deposited under American Type Culture Collection Accession Number ATCC HB-11894 (hybridoma 1A3.3.13) or HB-11895 (hybridoma 5D5.11.6) and substantially a human consensus sequence (e.g., substantially the human consensus framework (FR) residues of human heavy chain subgroup III ($V_H$III)). In one embodiment, the antibody further comprises the H chain CDR1 sequence and/or CDR2 sequence of the monoclonal antibody produced by the hybridoma cell line deposited under American Type Culture Collection Accession Number ATCC HB-11894 (hybridoma 1A3.3.13) or HB-11895 (hybridoma 5D5.11.6). In another embodiment, the preceding antibody comprises the L chain CDR1 sequence, CDR2 sequence and/or CDR3 sequence of the monoclonal antibody produced by the hybridoma cell line deposited under American Type Culture Collection Accession Number ATCC HB-11894 (hybridoma 1A3.3.13) or HB-11895 (hybridoma 5D5.11.6) with substantially the human consensus framework (FR) residues of human light chain K subgroup I (VκI).

In one embodiment, an antibody fragment of the invention comprises an antigen binding arm comprising a heavy chain variable domain having the sequence:
QVQLQQSGPELVRPGASVKMSCRASGUT-
FTSYWLHWVKQRPGQGL EWIGMIDPSNSDTR-

FNPNFKDKATLNVDRSSNTAYMLLSSLTSADSA VYYCATYGSYVSPLDYWGQGTSVTVSS (SEQ ID NO:7)

In one embodiment, an antibody fragment of the invention comprises an antigen binding arm comprising a light chain variable domain having the sequence:

DIMMSQSPSSLTVSVGEKVTVSCKSSQS-LLYTSSQKNYLAWYQQKPGQSPKL LIYWASTRES-GVPDRFTGSGSGTDFTLTITSVKAD-DLAVYYCQQYYAYPWTFGGGTK LEIK (SEQ ID NO:8)

Yet in other instances, it may be advantageous to have a c-met antagonist that does not interfere with binding of a ligand (such as HGF) to c-met. Accordingly, in some embodiments, an antagonist of the invention does not bind a ligand (such as HGF) binding site on c-met. In another embodiment, an antagonist of the invention does not substantially inhibit ligand (e.g., HGF) binding to c-met. In one embodiment, an antagonist of the invention does not substantially compete with a ligand (e.g., HGF) for binding to c-met. In one example, an antagonist of the invention can be used in conjunction with one or more other antagonists, wherein the antagonists are targeted at different processes and/or functions within the HGF/c-met axis. Thus, in one embodiment, a c-met antagonist of the invention binds to an epitope on c-met distinct from an epitope to which another c-met antagonist, such as the Fab fragment of the monoclonal antibody produced by the hybridoma cell line deposited under American Type Culture Collection Accession Number ATCC HB-11894 (hybridoma 1A3.3.13) or HB-11895 (hybridoma 5D5.11.6), binds. In another embodiment, a c-met antagonist of the invention is distinct from (i.e., it is not) a Fab fragment of the monoclonal antibody produced by the hybridoma cell line deposited under American Type Culture Collection Accession Number ATCC HB-11894 (hybridoma 1A3.3.13) or HB-11895 (hybridoma 5D5.11.6). In one embodiment, a c-met antagonist of the invention does not comprise a c-met binding sequence of an antibody produced by the hybridoma cell line deposited under American Type Culture Collection Accession Number ATCC HB-11894 (hybridoma 1A3.3.13) or HB-11895 (hybridoma 5D5.11.6). In one embodiment, an antagonist of the invention inhibits c-met activity but does not bind to a wild-type juxtamembrane domain of c-met.

In one embodiment of a c-met antagonist of the invention, binding of the antagonist to c-met inhibits c-met activation by HGF. In one embodiment of a c-met antagonist of the invention, binding of the antagonist to c-met in a cell inhibits proliferation, scattering, morphogenesis and/or motility of the cell. In one embodiment, a c-met antagonist of the invention binds to hyperstabilized c-met in a cell, resulting in cell death. For example, in one embodiment, the antagonist is linked to a toxin as described herein.

In some embodiments, a c-met antagonist of the invention is or comprises a peptide (e.g., an oligopeptide), antibody, antibody fragment, aptamer, oligonucleotide (e.g., antisense oligonucleotide), inhibitory RNA or a combination thereof.

In some embodiments, a c-met antagonist of the invention is obtained by a screening or identification method of the invention as described herein.

In another aspect, the invention provides methods for screening for or identifying a c-met antagonist. In one example, said methods comprise contacting a candidate substance with a target molecule comprising at least a portion of hyperstabilized c-met, whereby a substance that specifically binds said target molecule is selected (as a c-met antagonist). In one embodiment, the methods further comprises determining that a selected candidate substance specifically binds to a mutated region of hyperstabilized c-met. For example, if the target molecule comprises a polypeptide, a selected candidate substance should specifically bind to an epitope comprising a mutated position (or region) of hyperstabilized c-met. In another example, if the target molecule comprises a nucleic acid encoding at least a portion of hyperstabilized c-met, a selected candidate substance should specifically inhibit expression of hyperstabilized c-met protein from a nucleic acid encoding hyperstabilized c-met. In some embodiments, screening methods of the invention further comprise contacting a selected substance with a cell expressing hyperstabilized c-met, wherein inhibition of c-met activity in the cell is assessed (e.g., wherein extent of downstream c-met signaling (e.g., MAPK phosphorylation) is detected or quantitated). Inhibition of c-met signaling activity can be assayed in a variety of ways known in the art, and based on any of a variety of criteria known in the art, some of which are described in greater detail herein. For example, inhibition of c-met signaling activity may be indicated by a decrease in amount of c-met activation, which may in turn be indicated by, for instance, amount of c-met-associated cell signaling within a cell. Cell signaling can be assessed by a variety of methods and based on a variety of criteria, which are known in the art, some of which are described herein. For example, occurrence of cell signaling in the HGF/c-met pathway can manifest biologically in the form of change in phosphorylation of target molecules in the signaling pathway. Thus, e.g., amount of protein phosphorylation associated with one or more known phosphorylation targets in the HGF/c-met pathway could be measured. Examples of such phosphorylation targets include c-met itself and mitogen activated protein kinase (MAPK).

In one aspect, the invention provides compositions comprising one or more antagonists of the invention and a carrier. In one embodiment, the carrier is pharmaceutically acceptable.

In one aspect, the invention provides nucleic acids encoding a c-met antagonist of the invention. In one embodiment, a nucleic acid of the invention encodes a c-met antagonist which is or comprises a polypeptide (e.g., an oligopeptide). In one embodiment, a nucleic acid of the invention encodes a c-met antagonist which is or comprises an antibody or fragment thereof. In one embodiment, a nucleic acid of the invention is an aptamer. In one embodiment, a nucleic acid of the invention is an antisense oligonucleotide. In one embodiment, a nucleic acid of the invention is an inhibitory RNA (e.g., small interfering RNA).

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antagonist of the invention. For example, the invention provides a method of making a c-met antagonist which is or comprises an antibody (or fragment thereof), said method comprising expressing in a suitable host cell a recombinant vector of the invention encoding said antibody (or fragment thereof), and recovering said antibody. In another example, the invention provides a method of making a c-met antagonist which is or comprises a polypeptide (such as an oligopeptide), said method comprising expressing in a suitable host cell a recombinant vector of the invention encoding said polypeptide (such as an oligopeptide), and recovering said polypeptide (such as an oligopeptide).

In one aspect, the invention provides an article of manufacture comprising a container; and a composition contained within the container, wherein the composition comprises one or more c-met antagonists of the invention. In one embodiment, the composition comprises a nucleic acid of the invention. In one embodiment, a composition comprising antagonist further comprises a carrier, which in some embodiments is pharmaceutically acceptable. In one embodiment, an article of manufacture of the invention further comprises instructions for administering the composition (e.g., the antagonist) to a subject.

In one aspect, the invention provides a kit comprising a first container comprising a composition comprising one or more c-met antagonists of the invention; and a second container comprising a buffer. In one embodiment, the buffer is pharmaceutically acceptable. In one embodiment, a composition comprising antagonist further comprises a carrier, which in some embodiments is pharmaceutically acceptable. In one embodiment, a kit further comprises instructions for administering the composition (e.g., the antagonist) to a subject.

In one aspect, the invention provides use of a c-met antagonist of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder. The c-met antagonist can be of any form described herein, including antibody, antibody fragment, polypeptide (e.g., an oligopeptide), nucleic acid (e.g., an oligonucleotide, such as an antisense oligonucleotide, inhibitory RNA), an aptamer, or combination thereof.

In one aspect, the invention provides use of a nucleic acid of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an expression vector of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a host cell of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a kit of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

The invention provides methods and compositions useful for modulating disease states associated with dysregulation of the HGF/c-met signaling axis associated with delayed down-regulation of c-met. The HGF/c-met signaling pathway is involved in multiple biological and physiological functions, including, e.g., cell proliferation and angiogenesis. Thus, in one aspect, the invention provides a method comprising administering to a subject an antagonist that targets hyperstabilized c-met, whereby HGF/c-met signaling is modulated.

In one aspect, the invention provides a method of treating a tumor in a subject, said method comprising administering an antagonist of the invention to a subject, whereby the tumor is treated. In one embodiment, the tumor is determined to comprise hyperstabilized c-met. In one embodiment, the tumor is determined to comprise mutant c-met comprising deletion of at least a portion of exon 14.

In one embodiment of methods of the invention, a c-met inhibitor of the invention is administered in conjunction with an agent that induces and/or enhances receptor protein degradation.

In one aspect, the invention provides a method of inhibiting c-met activated cell proliferation, said method comprising contacting a cell or tissue with an effective amount of a c-met antagonist of the invention, whereby cell proliferation associated with c-met activation is inhibited.

In one aspect, the invention provides a method of treating a pathological condition associated with dysregulation of c-met activation in a subject, said method comprising administering to the subject an effective amount of a c-met antagonist of the invention, whereby said condition is treated.

In one aspect, the invention provides a method of inhibiting the growth of a cell that expresses c-met or hepatocyte growth factor, or both, said method comprising contacting said cell with a c-met antagonist of the invention thereby causing an inhibition of growth of said cell. In one embodiment, the cell is contacted by HGF expressed by a different cell (e.g., through a paracrine effect).

In one aspect, the invention provides a method of therapeutically treating a mammal having a cancerous tumor comprising a cell that expresses c-met or hepatocyte growth factor, or both, said method comprising administering to said mammal an effective amount of a c-met antagonist of the invention, thereby effectively treating said mammal. In one embodiment, the cell is contacted by HGF expressed by a different cell (e.g., through a paracrine effect).

In one aspect, the invention provides a method for treating or preventing a cell proliferative disorder associated with increased expression or activity of c-met or hepatocyte growth, or both, said method comprising administering to a subject an effective amount of a c-met antagonist of the invention, thereby effectively treating or preventing said cell proliferative disorder. In one embodiment, said proliferative disorder is cancer.

In one aspect, the invention provides a method for inhibiting the growth of a cell, wherein growth of said cell is at least in part dependent upon a growth potentiating effect of c-met or hepatocyte growth factor, or both, said method comprising contacting said cell with an effective amount of a c-met antagonist of the invention, thereby inhibiting the growth of said cell. In one embodiment, the cell is contacted by HGF expressed by a different cell (e.g., through a paracrine effect).

In one aspect, the invention provides a method of therapeutically treating a tumor in a mammal, wherein the growth of said tumor is at least in part dependent upon a growth potentiating effect of c-met or hepatocyte growth factor, or both, said method comprising contacting said cell with an effective amount of a c-met antagonist of the invention, thereby effectively treating said tumor. In one embodiment, the cell is contacted by HGF expressed by a different cell (e.g., through a paracrine effect).

Methods of the invention can be used to affect any suitable pathological state, for example, cells and/or tissues associated with dysregulation of the HGF/c-met signaling pathway. In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell (e.g., of the thyroid gland), a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, aprostate cancer cell, a gastric carcinoma cell, a head and neck squamous carcinoma cell, a lymphoma cell, a melanoma cell and a leukemia cell. In one embodiment, a cell that is targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell.

Methods of the invention can further comprise additional treatment steps. For example, in one embodiment, a method further comprises a step wherein a targeted cell and/or tissue (e.g., a cancer cell) is exposed to radiation treatment and/or a chemotherapeutic agent.

As described herein, c-met activation is an important biological process the dysregulation of which leads to numerous pathological conditions. Accordingly, in one embodiment of methods of the invention, a cell that is targeted (e.g., a cancer cell) is one in which activation of c-met is enhanced as compared to a normal cell of the same tissue origin. In one embodiment, a method of the invention causes the death of a targeted cell. For example, contact with an antagonist of the invention may result in a cell's inability to signal through the c-met pathway, which results in cell death or inhibition of cell growth. In another example, an antagonist of the invention targets a linked toxin to a cell expressing hyperstabilized c-met.

Dysregulation of c-met activation (and thus signaling) can result from a number of cellular changes, including, for example, overexpression of HGF (c-met's cognate ligand) and/or c-met itself (due to delayed down-regulation/degradation, increased expression levels, etc.). Accordingly, in some embodiments, a method of the invention comprises targeting a cell wherein c-met or hepatoctye growth factor, or both, is more abundantly expressed by said cell (e.g., a cancer cell) as compared to a normal cell of the same tissue origin. A c-met-expressing cell can be regulated by HGF from a variety of sources, i.e. in an autocrine or paracrine manner. For example, in one embodiment of methods of the invention, a targeted cell is contacted/bound by hepatocyte growth factor expressed in/by a different cell (e.g., via a paracrine effect). Said different cell can be of the same or of a different tissue origin relative to a targeted cell. In one embodiment, a targeted cell is contacted/bound by HGF expressed by the targeted cell itself (e.g., via an autocrine effect/loop). C-met activation and/or signaling can also occur independent of ligand. Hence, in one embodiment of methods of the invention, c-met activation in a targeted cell occurs independent of ligand.

In one embodiment of methods of the invention, the methods further comprise a step of determining whether a tumor cell comprises hyperstabilized c-met (e.g., by detecting a polynucleotide or polypeptide mutation, as described herein).

BRIEF DESCRIPTION OF THE DRAWINGS

FIG. 1 depicts illustrative intronic mutations flanking exon 14 of Met. A schematic representation of Met exon 14 showing the corresponding nucleic acid (NM_000245) deletions and/or point mutations (light grey text) with respect to the intron/exon structure. (A) H596, lung cancer cell line. (B) pat. 14, patient 14 lung tumor specimen. (C) pat. 16, patient 16 lung tumor specimen. For reference, in tumor H596, there is a point mutation from G to T at position marked +1 in (A). In tumor Pat 14, there is a deletion of the sequence from position marked −27 to −6 in (B). In tumor Pat 16, there is a deletion of the sequence from position marked 3195 to +7 in (C).

FIG. 2. Delayed down regulation of hyperstabilized c-met is associated with activation of Met and MAPK. (A) 293 cells co-transfected with Met constructs and Cbl-flag were immunoprecipitated (IP) with V5 or Cbl antibodies followed by immunoblotting (IB) with V5, flag, or P-Tyr antibodies. Lysates were probed with flag or Cbl antibodies. (B) 293 cells were transfected with Met constructs followed by IP of endogenous Cbl. Immunoblotting with V5 antibody shows that Met WT, but not MetΔEx14 co-IPs with endogenous Cbl. The membrane was stripped and reprobed with Y1003, YY1234/1235, Y1349, or Y1365 phospho-specific antibodies. (C) Lysates from transient transfection of 293 cells were immunoprecipitated with V5 antibody and immunoblotted with ubiquitin antibody to detect ubiquitinated Met. The membrane was stripped and reprobed with V5 antibody to detect the presence of Met. Lysates were probed with flag or actin antibodies to detect Cbl-flag or actin for equivalent expression. (D) 293 cells were transfected with the indicated constructs and treated with 10 μg/ml cycloheximide. Lysates were probed with V5 antibody or actin. (E) Serum-starved lung cancer cell lines were stimulated for 10 minutes with 50 ng/ml rhuHGF, then rinsed and returned to serum-free media. Lysates were collected at the indicated times and immunoblotted for P-Met (Y1230/Y1234/Y1235), Met, P-MAPK, MAPK, P-Akt, or Akt. (F) Rat 1A stable clones were serum-starved and treated for 10 minutes with an agonistic Met monoclonal antibody 3D6 (5 μg/ml), rinsed with PBS, and returned to serum-free media. At the indicated times, lysates were obtained and immunoblotted for P-MAPK, MAPK, P-Akt, or Akt.

FIG. 3. Enhanced ligand-dependent proliferative potential in cell lines harboring the Met juxtamembrane deletion (A) HGF-stimulated growth in a panel of NSCLC cell lines was determined after a 72 hour culture in the presence or absence of 50 ng/ml rhuHGF. Results are depicted as a stimulation index (SI), as determined from a minimum of three separate experiments. (B) Growth curves of subcutaneously inoculated Rat 1A stable cell lines expressing vector, Met WT, Met ΔEx14, in each case in the presence or absence of an HGF agonist antibody (3D6) in nude mice.

FIG. 4. Inhibition of ligand-dependent Met signaling and growth in H596 cells with an anti-Met mAb, OA-5D5. (A) Serum-starved H226 or H596 cells were incubated with OA-5D5 for 30 minutes at the indicated concentrations and then stimulated with 100 ng/ml rhuHGF for 15 minutes. Lysates were obtained and immunoblotted for P-Met (Y1234/Y1235), Met, P-Akt, Akt, P-MAPK, or MAPK. (B) Cells were treated with OA-5D5 or a control Ig at the indicated concentrations in the presence or absence of 50 ng/ml rhuHGF and cell viability was determined after 72 hours.

FIG. 5. Quantification of phospho-kinase to kinase ratios in Rat1A stable Met cell lines. The ratio of P-MAPK:MAPK (left) and P-Akt:Akt (right) was quantified using Odyssey infrared scanner that detects AlexaFluor680 and IR Dye800 conjugated secondary antibodies.

FIG. 6. Quantification of phospho-kinase to kinase ratios in H596 and H226 cells treated with OA-5D5. The ratio of P-Met:Met, P-Akt:Akt, or P-MAPK:MAPK for each cell line was quantified using Odyssey infrared scanner that detects AlexaFluor680 and IRDye800 conjugated secondary antibodies.

FIG. 7 depicts illustrative cis-acting splicing elements expected to regulate splicing of human c-met exon 14. It is expected that a mutation at one or more positions within these elements would have a negative impact on wild type splicing of exon 14.

FIG. 8 depicts wild-type human c-met protein sequence based on RefSeq. NM_000245 (SEQ ID NO:17).

FIG. 9 depicts light and heavy chain variable domain sequences for the OA-5D5 antibody referred to in the Examples;

MODES FOR CARRYING OUT THE INVENTION

The invention provides methods, compositions, kits and articles of manufacture for identifying inhibitors of the HGF/c-met signaling pathway (in particular, inhibitors of hyperstabilized c-met), and methods of using such inhibitors.

Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988).

Definitions

The term "hyperstabilized c-met", and variations thereof, as used herein, refers to a naturally-occuring mutant human c-met that is degraded/down-regulated at a rate that is detectably slower than that of a wild-type c-met. Methods of comparing degration/down-regulation rates between wild-type c-met and a hyperstabilized c-met would be evident to one skilled in the art, including, for example, as described in the Examples below. In one instance, delayed degradation/down-regulation is assessed based on quantitating receptor protein levels in a cell. In another instance, delayed degradation/down-regulation is determined based detection of a mutation in a c-met site that is associated with Cbl binding to c-met. In one instance, the mutation is in a c-met site that is associated with c-met ubiquitination (e.g., in c-met exon 14) and receptor protein degradation/down-regulation. These mutations can arise in any form that results in expression of a mutated c-met protein that is degraded/down-regulated at a slower rate than wild type c-met, wherein the mutated c-met protein is capable of wild-type c-met-associated activity (e.g., phosphorylating downstream molecules such as MAPK, stimulating cell proliferation and/or induction of tumorigenic events). For example, these mutations include those that are associated with expression of a functional, in-frame c-met splice variant lacking at least a portion of exon 14 that is associated with receptor protein degradation/down-regulation. Illustrative examples of mutations include those found in a splicing element as depicted in FIGS. 1 and 7. In one embodiment, presence of a hyperstabilized c-met protein of the invention in a cell is associated with prolonged and/or increased phosphorylation of downstream molecules in the HGF/c-met pathway as compared with a similar amount of wild-type c-met protein in a cell;

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "hepatocyte growth factor" or "HGF", as used herein, refers, unless indicated otherwise, to any native or variant (whether native or synthetic) HGF polypeptide that is capable of activating the HGF/c-met signaling pathway under conditions that permit such process to occur. The term "wild type HGF" generally refers to a polypeptide comprising the amino acid sequence of a naturally occurring HGF protein. Thet term "wild type HGF sequence" generally refers to an amino acid sequence found in a naturally occurring HGF. C-met (or Met) is a known receptor for HGF through which HGF intracellular signaling is biologically effectuated. A wild type human c-met protein sequence based on RefSeq NM_000245 is depicted in FIG. 8.

The terms "splice site", "splice junction", "branch point", "polypyrimidine tract", as used herein, refer to the meaning known in the art in the context of mammalian, in particular human, RNA splicing. See, e.g., Pagani & Baralle, Nature Reviews: Genetics (2004), 5:389-396, and references cited therein. For convenient reference, one embodiment of sequences for c-met RNA splicing elements is illustratively set forth in FIG. 7.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "hypervariable region", "HVR", or "HV", when used herein refers to the regions of an antibody variable domain which are hypervariable in sequence and/or form structurally defined loops. The letters "HC" and "LC" preceding the term "HVR" or "HV" refers, respectively, to HVR or HV of a heavy chain and light chain. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
| --- | --- | --- | --- | --- |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

"Framework" or "FR" residues are those variable domain residues other than the hypervariable region residues as herein defined.

The "variable region" or "variable domain" of an antibody refers to the amino-terminal domains of heavy or light chain of the antibody. These domains are generally the most variable parts of an antibody and contain the antigen-binding sites.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs/HVRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR/HVR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The term "cytotoxic agent" as used herein refers to a substance that inhibits or prevents the function of cells and/or causes destruction of cells. The term is intended to include radioactive isotopes (e.g. $At^{211}$, $I^{311}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other antiandrogens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC.®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl) benzenesulfonamide; and pharmaceutically acceptable salts, acids or derivatives of any of the above.

A "blocking" antibody or an "antagonist" antibody is one which inhibits or reduces biological activity of the antigen it binds. Such blocking can occur by any means, e.g. by interfering with protein-protein interaction such as ligand binding to a receptor. In on embodiment, blocking antibodies or antagonist antibodies substantially or completely inhibit the biological activity of the antigen.

The terms "cancer" and "cancerous" refer to or describe the physiological condition in mammals that is typically characterized by unregulated cell growth/proliferation. Examples of cancer include but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, modulator molecules and methods of the invention are used to delay development of a disease or disorder.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Compositions and Methods of the Invention

A. C-met Antagonist Antibodies

In one embodiment, the invention provides C-met antagonist antibodies which may find use herein as therapeutic and/or diagnostic agents. Exemplary antibodies include polyclonal, monoclonal, humanized, bispecific, and heteroconjugate antibodies. Aspects of generating, identifying, characterizing, modifying and producing antibodies are well established in the art, e.g., as described in US Pat. Appl. Pub. No. 2005/0042216 from paragraphs 522 through 563, 604 through 608, and 617 through 688.

The C-met antagonist antibodies disclosed herein can be formulated in any suitable form for delivery to a target cell/tissue. For example, the antibodies may be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. C-met Antagonist Polypeptides

In one aspect, a C-met antagonist of the invention comprises a polypeptide. In one embodiment, the antagonist polypeptide binds to and/or antagonizes hyperstabilized c-met protein in a cell. In one embodiment, the polypeptides bind, preferably specifically, to hyperstabilized c-met. The polypeptides may be chemically synthesized using known peptide synthesis methodology or may be prepared and purified using recombinant technology. In one embodiment, a C-met antagonist polypeptide is at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such polypeptides are capable of inhibiting hyperstabilized c-met activity. These polypeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223, 409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

Bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene*, 215: 439 (1998); Zhu et al., *Cancer Research*, 58(15): 3209-3214 (1998); Jiang et al., *Infection & Immunity*, 65(11): 4770-4777 (1997); Ren et al., *Gene*, 195(2):303-311 (1997); Ren, *Protein Sci.*, 5: 1833 (1996); Efimov et al., *Virus Genes*, 10: 173 (1995)) and T7 phage display systems (Smith and Scott, *Methods in Enzymology*, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties.

Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphlylococcus aureus* protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

Methods of generating, identifying, characterizing, modifying and producing antagonist polypeptides are well established in the art, e.g., as described in US Pat. Appl. Pub. No. 2005/0042216 from paragraphs 606 through 608, 614 through 688.

In one embodiment, polypeptides for antagonizing hyperstabilized c-met activity can be designed based on hyperstabilized c-met protein structure, e.g. by screening based on a target antigen comprising a mutant c-met juxtamembrane sequence comprising deletion of at least a portion of exon 14 as described herein. For example, a target antigen can comprise a polypeptide comprising a sequence resulting from in-frame splicing of exon 13 and 15 of c-met.

C. Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19): 1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogarnicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is tested for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is tested for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7): 778-784) and are under therapeutic development.

Chemotherapeutic agents useful in the generation of immunoconjugates are described herein (above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolostatins, aurostatins, a trichothecene, and CC1065, and the derivatives of these toxins that have toxin activity, are also contemplated herein.

Maytansine and Maytansinoids

In some embodiments, the immunoconjugate comprises an antibody of the invention conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Exemplary embodiments of maytansinoid drug moieities include: DM1; DM3; and DM4. Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates can be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

An exemplary auristatin embodiments are MMAE and MMAF. Additional exemplary embodiments comprising MMAE or MMAF and various linker components (described further herein) Ab-MC-vc-PAB-MMAF, Ab-MC-vc-PAB-MMAE, Ab-MC-MMAE and Ab-MC-MMAF.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 15:859-863. See also Doronina (2003) Nat Biotechnol 21(7): 778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad \text{I}$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Exemplary linker component structures are shown below (wherein the wavy line indicates sites of covalent attachment to other components of the ADC):

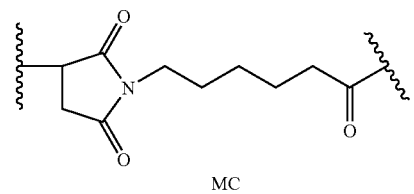

MC

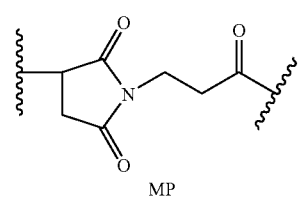

MP

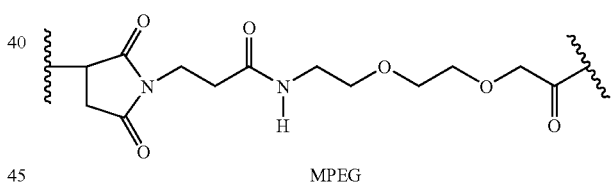

MPEG

Additional exemplary linker components and abbreviations include (wherein the antibody (Ab) and linker are depicted, and p is 1 to about 8):

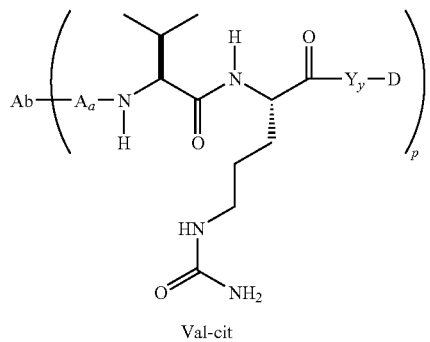

Val-cit

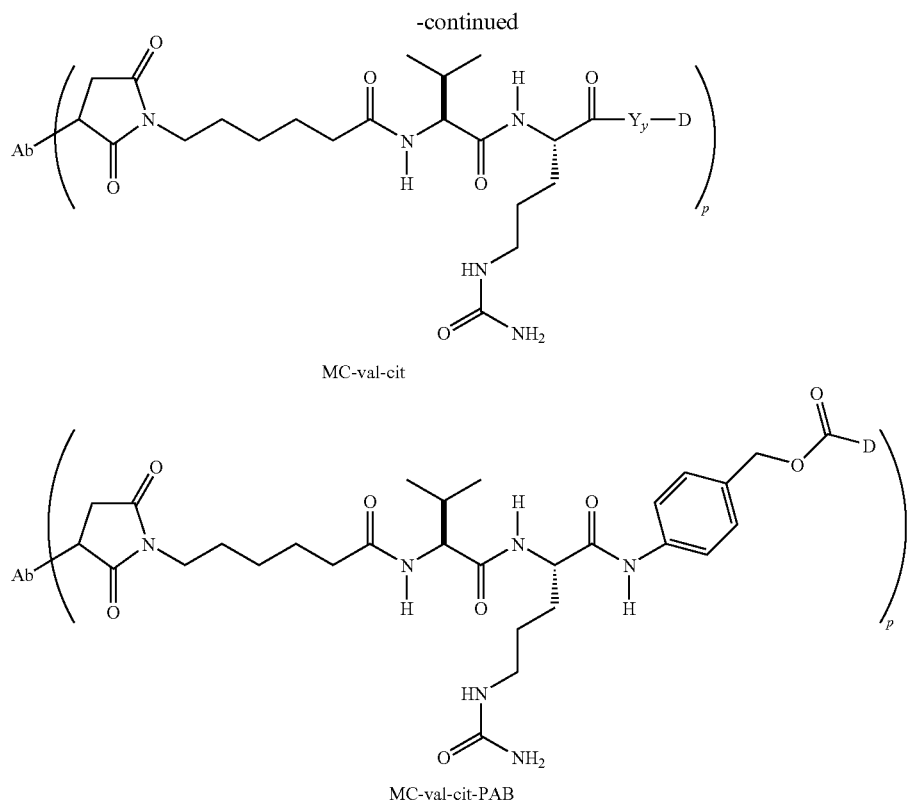

MC-val-cit

MC-val-cit-PAB

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic subsituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362, 852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody (Ab)-MC-MMAE may be prepared by conjugation of any of the antibodies provided herein with MC-MMAE as follows. Antibody, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice. The drug linker reagent, maleimidocaproyl-monomethyl auristatin E (MMAE), i.e. MC-MMAE, dissolved in DMSO, is diluted in acetonitrile and water at known concentration, and added to the chilled reduced antibody 2H9 in PBS. After about one hour, an excess of maleimide is added to quench the reaction and cap any unreacted antibody thiol groups. The reaction mixture is concentrated by centrifugal ultrafiltration and 2H9-MC-MMAE is purified and desalted by elution through G25 resin in PBS, filtered through 0.2 μm filters under sterile conditions, and frozen for storage.

Antibody-MC-MMAF may be prepared by conjugation of any of the antibodies provided herein with MC-MMAF following the protocol provided for preparation of Ab-MC-MMAE.

Antibody-MC-val-cit-PAB-MMAE is prepared by conjugation of any of the antibodies provided herein with MC-val-cit-PAB-MMAE following the protocol provided for preparation of Ab-MC-MMAE.

Antibody-MC-val-cit-PAB-MMAF is prepared by conjugation of any of the antibodies provided herein with MC-val-cit-PAB-MMAF following the protocol provided for preparation of Ab-MC-MMAE.

Antibody-SMCC-DM1 is prepared by conjugation of any of the antibodies provided herein with SMCC-DM1 as follows. Purified antibody is derivatized with (Succinimidyl 4-(N-maleimidomethyl)cyclohexane-1-carboxylate (SMCC, Pierce Biotechnology, Inc) to introduce the SMCC linker. Specifically, antibody is treated at 20 mg/mL in 50 mM potassium phosphate/50 mM sodium chloride/2 mM EDTA, pH 6.5 with 7.5 molar equivalents of SMCC (20 mM in DMSO, 6.7 mg/mL). After stirring for 2 hours under argon at ambient temperature, the reaction mixture is filtered through a Sephadex G25 column equilibrated with 50 mM potassium phosphate/50 mM sodium chloride/2 mM EDTA, pH 6.5. Antibody containing fractions are pooled and assayed.

Antibody-SMCC prepared thus is diluted with 50 mM potassium phosphate/50 mM sodium chloride/2 mM EDTA, pH 6.5, to a final concentration of about 10 mg/ml, and reacted with a 10 mM solution of DM1 in dimethylacetamide. The reaction is stirred at ambient temperature under argon 16.5 hours. The conjugation reaction mixture is filtered through a Sephadex G25 gel filtration column (1.5×4.9 cm) with 1×PBS at pH 6.5. The DM1 drug to antibody ratio (p) may be about 2 to 5, as measured by the absorbance at 252 nm and at 280 nm.

Ab-SPP-DM1 is prepared by conjugation of any of the antibodies provided herein with SPP-DM1 as follows. Purified antibody is derivatized with N-succinimidyl-4-(2-pyridylthio)pentanoate to introduce dithiopyridyl groups. Antibody (376.0 mg, 8 mg/mL) in 44.7 mL of 50 mM potassium phosphate buffer (pH 6.5) containing NaCl (50 mM) and EDTA (1 mM) is treated with SPP (5.3 molar equivalents in 2.3 mL ethanol). After incubation for 90 minutes under argon at ambient temperature, the reaction mixture is gel filtered through a ephadex G25 column equilibrated with 35 mM sodium citrate, 154 mM NaCl, 2 mM EDTA. Antibody containing fractions were pooled and assayed. The degree of modification of the antibody is determined as described above.

Antibody-SPP-Py (about 10 μmoles of releasable 2-thiopyridine groups) is diluted with the above 35 mM sodium citrate buffer, pH 6.5, to a final concentration of about 2.5 mg/mL. DM1 (1.7 equivalents, 17 μmoles) in 3.0 mM dimethylacetamide (DMA, 3% v/v in the final reaction mixture) is then added to the antibody solution. The reaction proceeds at ambient temperature under argon for about 20 hours. The reaction is loaded on a Sephacryl S300 gel filtration column (5.0 cm×90.0 cm, 1.77 L) equilibrated with 35 mM sodium citrate, 154 mM NaCl, pH 6.5. The flow rate may be about 5.0 mL/min and 65 fractions (20.0 mL each) are collected. The number of DM1 drug molecules linked per antibody molecule (p') is determined by measuring the absorbance at 252 nm and 280 nm, and may be about 2 to 4 DM1 drug moieties per 2H9 antibody.

Antibody-BMPEO-DM1 is prepared by conjugation of any of the antibodies provided herein with BMPEO-DM1 as follows. The antibody is modified by the bis-maleimido reagent BM(PEO)4 (Pierce Chemical), leaving an unreacted maleimido group on the surface of the antibody. This may be accomplished by dissolving BM(PEO)4 in a 50% ethanol/water mixture to a concentration of 10 mM and adding a tenfold molar excess to a solution containing antibody in phosphate buffered saline at a concentration of approximately 1.6 mg/ml (10 micromolar) and allowing it to react for 1 hour to form antibody-linker intermediate, 2H9-BMPEO. Excess BM(PEO)4 is removed by gel filtration (HiTrap column, Pharmacia) in 30 mM citrate, pH 6 with 150 mM NaCl buffer. An approximate 10 fold molar excess DM1 is dissolved in dimethyl acetamide (DMA) and added to the 2H9-BMPEO intermediate. Dimethyl formamide (DMF) may also be employed to dissolve the drug moiety reagent. The reaction mixture is allowed to react overnight before gel filtration or dialysis into PBS to remove unreacted DM1. Gel filtration on S200 columns in PBS was used to remove high molecular weight aggregates and furnish purified 2H9-BMPEO-DM1.

D. C-met Antagonists Comprising Nucleic Acids

In one aspect, a C-met antagonist of the invention comprises a nucleic acid molecule. For example, the nucleic acid molecule may comprise an antisense oligonucleotide, an inhibitory/interfering RNA (e.g., a small inhibitory/interfering RNA (siRNA)), or an aptamer. Methods for screening for, identifying and making these nucleic acid modulators are known in the art.

For example, siRNAs have proven capable of modulating gene expression where traditional antagonists such as small molecules or antibodies have failed. (Shi Y., Trends in Genetics 19(1):9-12 (2003)). In vitro synthesized, double stranded RNAs that are fewer than 30 nucleotides in length (e.g., about 15 to 25, 17 to 20, 18 to 20, 19 to 20, or 21 to 23 nucleotides) can act as interfering RNAs (iRNAs) and can specifically inhibit gene expression (see, e.g., Fire A., Trends in Genetics (1999), 391; 806-810; U.S. Pat. appln. Ser. Nos. 09/821,832, 09/215,257; U.S. Pat. No. 6,506,559; PCT/US01/10188; European Appln. Ser. No. 00126325). These iRNAs are believed to act at least in part by mediating degradation of their target RNAs. However, since they are under 30 nucloutides in length, they do not trigger a cell antiviral defense mechanism. Such mechanisms include interferon production, and a general shutdown of host cell protein synthesis. Practically, siRNAs can be synthesized and then cloned into DNA vectors. Such vectors can be transfected and made to express the siRNA at high levels. The high level of siRNA expression is used to "knockdown" or significantly reduce the amount of protein produced in a cell, and thus it is useful in cellular settings where overexpression of a protein is believed to be linked to a pathological disorder.

Aptamers are nucleic acid molecules that are capable of binding to a target molecule, such as a hyperstabilized c-met protein. The generation and therapeutic use of aptamers are well established in the art. See, e.g., U.S. Pat. No. 5,475,096, and the therapeutic efficacy of Macugen® (Eyetech, New York) for treating age-related macular degeneration.

Anti-sense technology is well established in the art. Further details regarding this technology are provided hereinbelow.

E. Pharmaceutical Formulations

Therapeutic formulations of the C-met antagonists used in accordance with the invention are prepared for storage by mixing the C-met antagonist having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG).

The formulations herein may also contain more than one active compound as necessary for the particular indication being treated, preferably those with complementary activities that do not adversely affect each other. For example, in addition to a C-met antagonist, it may be desirable to include in the one formulation, an additional modulator, e.g., a second antibody which binds a different epitope on the hyperstabilized c-met protein, or an antibody to some other target. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

F. Treatment with a C-met Antagonist of the Invention

C-met antagonists of the invention have various non-therapeutic applications. The antagonists can be useful for staging or detecting hyperstabilized c-met-expressing diseases (e.g., in radioimaging). The antibodies, oligopeptides and aptamers can also be useful for purification or immunoprecipitation of hyperstabilized c-met from cells, for detection and quantitation of hyperstabilized c-met in vitro, e.g., in an ELISA or a Western blot, and to modulate cellular events in a population of cells.

Currently, depending on the stage of the cancer, cancer treatment involves one or a combination of the following therapies: surgery to remove the cancerous tissue, radiation therapy, and chemotherapy. Therapy comprising C-met antagonists may be especially desirable in elderly patients who do not tolerate the toxicity and side effects of chemotherapy well and in metastatic disease where radiation therapy has limited usefulness. For therapeutic applications, the C-met antagonists can be used alone, or in combination therapy with, e.g., hormones, antiangiogens, or radiolabelled compounds, or with surgery, cryotherapy, and/or radiotherapy. The C-met antagonists can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. The C-met antagonists would generally be administered with a therapeutically effective dose of the chemotherapeutic agent. In another embodiment, a C-met antagonist is administered in conjunction with chemotherapy to reduce side-effects reslting from the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

The C-met antagonists are administered to a human patient, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic small molecule is preferred in one embodiment of the invention.

Other therapeutic regimens may be combined with the administration of the C-met antagonist. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect and/or reduction of unwanted side effects.

It may also be desirable to combine administration of the C-met antagonist, with administration of a therapeutic agent directed against another antigen associated with the particular pathological condition.

In another embodiment, the therapeutic treatment methods of the present invention involves the combined administration of a C-met antagonist molecule and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The C-met antagonist may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the C-met antagonist may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post C-met antagonist therapy. Suitable dosages for any of the above co-administered agents are those presently used and may be lowered due to the combined action (synergy) of the agent and C-met antagonist.

For the prevention or treatment of disease, the dosage and mode of administration will be chosen by the physician according to known criteria. The appropriate dosage of C-met antagonist will depend on the type of disease to be treated, as defined above, the severity and course of the disease, whether the C-met antagonist is administered for preventive or therapeutic purposes, previous therapy, the patient's clinical history and response to the C-met antagonist, and the discretion of the attending physician. The C-met antagonist is suitably administered to the patient at one time or over a series of treatments. In one embodiment, the C-met antagonist is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the C-met antagonist antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of a polypeptide modulator (e.g., polypeptide, antibody, etc.) to the patient, the invention contemplates administration of a modulator by gene therapy. Such administration of nucleic acid comprising/encoding the C-met antagonist is encompassed by the expression "administering a therapeutically effective amount of a C-met antagonist". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the C-met antagonist is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

In one embodiment, in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

C-met antagonist antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, and functional fragments thereof.

The invention provides a composition comprising a C-met antagonist, and a carrier. In a further embodiment, a composition can comprise a C-met antagonist in combination with other therapeutic agents such as cytotoxic or growth inhibitory agents, including chemotherapeutic agents. The invention also provides formulations comprising a C-met antagonist, and a carrier. In one embodiment, the formulation is a therapeutic formulation comprising a pharmaceutically acceptable carrier.

G. Articles of Manufacture and Kits

Another embodiment of the invention is an article of manufacture containing materials useful for the treatment of a disorder using a C-met antagonist. The article of manufacture comprises a container and a label or package insert on or associated with the container. Suitable containers include, for example, bottles, vials, syringes, etc. The containers may be formed from a variety of materials such as glass or plastic.

The container holds a composition which is effective for treating the condition and may have a sterile access port (for example the container may be an intravenous solution bag or a vial having a stopper pierceable by a hypodermic injection needle). At least one active agent in the composition is a C-met antagonist of the invention. The label or package insert indicates that the composition is used for treating a particular disorder. The label or package insert will further comprise instructions for administering the composition to the patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes. Kits can be provided which contain C-met antagonists of the invention for detection and quantitation of hyperstabilized c-met in vitro, e.g., in an ELISA or a Western blot. As with the article of manufacture, the kit comprises a container and a label or package insert on or associated with the container. The container holds a composition comprising at least one C-met antagonist of the invention. Additional containers may be included that contain, e.g., diluents and buffers, control antibodies. The label or package insert may provide a description of the composition as well as instructions for the intended in vitro or detection use.

H. C-met Antagonists Comprising Polypeptides, Nucleic Acids and Antibodies—Specific Forms and Applications In one embodiment, nucleic acids of the invention include antisense oligonucleotides/polynucleotides comprising a singe-stranded nucleic acid sequence (either RNA or DNA) capable of binding to endogenous hyperstabilized c-met-encoding nucleic acids. Antisense oligonucleotides, according to the present invention, comprise at least a fragment of the coding region of hyperstabilized c-met DNA. Such a fragment generally comprises at least about 14 nucleotides, preferably from about 14 to 30 nucleotides. The ability to derive an antisense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of a hyperstabilized c-met protein in cells. Antisense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other exemplary regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of antisense compounds useful for inhibiting expression of hyperstabilized c-met polypeptide include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Exemplary modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Exemplary oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other examples of antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Examples of antisense oligonucleotides incorporate phosphorothioate backbones and/or heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] described in the above referenced U.S. Pat. No. 5,489,677, and the amide backbones of the above referenced U.S. Pat. No. 5,602,240. Additional examples are antisense oligonucleotides having morpholino backbone structures of the above-referenced U.S. Pat. No. 5,034,506.

Modified oligonucleotides may also contain one or more substituted sugar moieties. Exemplary oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other exemplary antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One possible modification includes 2'-methoxyethoxy (2'-O—$CH_2$$CH_2$O$CH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$).

A further modification includes Locked Nucleic Acids (LNAs) in which the 2'-hydroxyl group is linked to the 3' or 4' carbon atom of the sugar ring thereby forming a bicyclic sugar moiety. The linkage can be a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other modifications include 2'-methoxy (2'-O—$CH_3$), 2'-aminopropoxy (2'-O$CH_2$$CH_2$$CH_2$ $NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$ or —$CH_2$—C≡CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido [5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley, & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are exemplary base substitutions, e.g., when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides comprises chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic-acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Exemplary chimeric antisense oligonucleotides incorporate at least one 2' modified sugar (preferably 2'-O—$(CH_2)_2$—O—$CH_3$) at the 3' terminal to confer nuclease resistance and a region with at least 4 contiguous 2'-H sugars to confer RNase H activity. Such compounds have also been referred to in the art as hybrids or gapmers. Exemplary gapmers have a region of 2' modified sugars (preferably 2'-O—$(CH_2)_2$—O—$CH_3$) at the 3'-terminal and at the 5' terminal separated by at least one region having at least 4 contiguous 2'-H sugars and may incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In an exemplary procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. In general, conjugation of the ligand binding molecule preferably does not substantially interfere with the ability of the ligand binding molecule to bind to its corresponding molecule or receptor, or block entry of the sense or antisense oligonucleotide or its conjugated version into the cell.

Alternatively, an antisense oligonucleotide may be introduced into a cell containing the target nucleic acid sequence by formation of an oligonucleotide-lipid complex, as described in WO 90/10448. The antisense oligonucleotide-lipid complex is preferably dissociated within the cell by an endogenous lipase.

Antisense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci USA* 87, 3410-3414 (1990). For review of gene marking and gene therapy protocols see Anderson et al., *Science* 256, 808-813 (1992).

C-met antagonist polypeptides and nucleic acid molecules of the invention may be used diagnostically for tissue typing, wherein hyperstabilized c-met polypeptides may be differentially expressed in one tissue as compared to another, preferably in a diseased tissue as compared to a normal tissue of the same tissue type.

This invention encompasses methods of screening compounds to identify those that modulate hyperstabilized c-met. Screening assays for antagonist drug candidates are designed to identify compounds that bind or complex with the hyperstabilized c-met polypeptide, or otherwise interfere with the interaction of the hyperstabilized c-met polypeptides with other cellular proteins, including e.g., inhibiting the expression of hyperstabilized c-met polypeptide from cells.

The assays can be performed in a variety of formats, including protein-protein binding assays, biochemical screening assays, immunoassays, and cell-based assays, which are well characterized in the art.

All assays for antagonists are common in that they call for contacting the drug candidate with a hyperstabilized c-met polypeptide under conditions and for a time sufficient to allow these two components to interact.

In binding assays, the interaction is binding and the complex formed can be isolated or detected in the reaction mixture. In a particular embodiment, the hyperstabilized c-met polypeptide or the drug candidate is immobilized on a solid phase, e.g., on a microtiter plate, by covalent or non-covalent attachments. Non-covalent attachment generally is accomplished by coating the solid surface with a solution of the hyperstabilized c-met polypeptide and drying. Alternatively, an immobilized antibody, e.g., a monoclonal antibody, specific for the hyperstabilized c-met polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a hyperstabilized c-met polypeptide, its interaction with hyperstabilized c-met can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of hyperstabilized c-met and other intra- or extracellular components can be tested as follows: usually a reaction mixture is prepared containing hyperstabilized c-met and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the compound to be screened for a particular activity may be added to a cell expressing hyperstabilized c-met, and the ability of the compound to inhibit the activity of interest indicates that the compound is an antagonist to the hyperstabilized c-met polypeptide. The hyperstabilized c-met polypeptide can be labeled, such as by radioactivity, such that the number of hyperstabilized c-met polypeptide molecules present on the cell can be used to determine the effectiveness of the potential antagonist.

A potential hyperstabilized c-met antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence which encodes the mature hyperstabilized c-met protein can be used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the hyperstabilized c-met polypeptide. The antisense RNA oligonucleotide hybridizes to the mRNA in vivo and blocks translation of the mRNA molecule into the hyperstabilized c-met polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the hyperstabilized c-met polypeptide. When antisense DNA is used, oligodeoxyribonucleotides derived from the translation-initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

In one embodiment, internalizing antibodies are preferred. Antibodies can possess certain characteristics, or modified to possess such characteristics, that enhance delivery of antibodies into cells. Techniques for achieving this are known in the art. In yet another embodiment, an antibody can be expressed in a target cell by introducing a nucleic acid capable of expressing the antibody into a targeted cell. See, e.g., U.S. Pat. Nos. 6,703,019; 6,329,173; and PCT Pub. No. 2003/077945. Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes. See, e.g., Chen et al., *Proc. Natl. Acad. Sci. USA* (1999), 96:4325-4329.

C-met antagonist antibodies of the invention can be any antibody that is capable of interfering with c-met activity. Some specific examples include an anti-c-met antibody comprising:

(a) at least one, two, three, four or five hypervariable region (HVR) sequences selected from the group consisting of:

(i) HVR-L1 comprising sequence A1-A17, wherein A1-A17 is KSSQSLLYTSSQKNYLA (SEQ ID NO:4)

(ii) HVR-L2 comprising sequence B1-B7, wherein B1-B7 is WASTRES (SEQ ID NO:5)

(iii) HVR-L3 comprising sequence C1-C9, wherein C1-C9 is QQYYAYPWT (SEQ ID NO:6)

(iv) HVR-H1 comprising sequence D1-D10, wherein D1-D10 is GYTFTSYWLH (SEQ ID NO.20)

(v) HVR-H2 comprising sequence E1-E18, wherein E1-E18 is GMIDPSNSDTRFNPNFKD (SEQ ID NO:21) and (vi) HVR-H3 comprising sequence F1-F11, wherein F1-F11 is XYGSYVSPLDY (SEQ ID NO:22) and X is not R;

and (b) at least one variant HVR, wherein the variant HVR sequence comprises modification of at least one residue of the sequence depicted in SEQ ID NOs:4, 5, 6, 20, 21 or 22. In one embodiment, HVR-L1 of an antibody of the invention comprises the sequence of (SEQ ID NO:4). In one embodiment, HVR-L2 of an antibody of the invention comprises the sequence of (SEQ ID NO:5). In one embodiment, HVR-L3 of an antibody of the invention comprises the sequence of (SEQ ID NO:6). In one embodiment, HVR-H1 of an antibody of the invention comprises the sequence of (SEQ ID NO:20). In one embodiment, HVR-H2 of an antibody of the invention comprises the sequence of (SEQ ID NO:21). In one embodiment, HVR-H3 of an antibody of the invention comprises the sequence of (SEQ ID NO:22). In one embodiment, HVR-H3 comprises TYGSYVSPLDY (SEQ ID NO:23). In one embodiment, HVR-H3 comprises SYGSYVSPLDY (SEQ ID NO:24). In one embodiment, an antibody of the invention comprising these sequences (in combination as described herein) is humanized or human.

In one aspect, the invention provides an antibody comprising one, two, three, four, five or six HVRs, wherein each HVR comprises, consists or consists essentially of a sequence selected from the group consisting of SEQ ID NOs:4, 5, 6, 20, 21, 22, 23 or 24, and wherein SEQ ID NO:4 corresponds to an HVR-L1, SEQ ID NO:5 corresponds to an HVR-L2, SEQ ID NO:6 corresponds to an HVR-L3, SEQ ID NO: 20 corresponds to an HVR-H1, SEQ ID NO:21 corresponds to an HVR-H2, and SEQ ID NOs: 22, 23 or 24 corresponds to an HVR-H3. In one embodiment, an antibody of the invention comprises HVR-L1, HVR-L2, HVR-L3; HVR-H1, HVR-H2, and HVR-H3, wherein each, in order, comprises SEQ ID NOs:4, 5, 6, 20, 21, and 23. In one embodiment, an antibody of the invention comprises HVR-L1, HVR-L2, HVR-L3, HVR-H1, HVR-H2, and HVR-H3, wherein each, in order, comprises SEQ ID NOs:4, 5, 6, 20, 21, and 24.

Variant HVRs in an antibody of the invention can have modifications of one or more residues within the HVR. In one embodiment, a HVR-L2 variant comprises 1-5 (1, 2, 3, 4 or 5) substitutions in any combination of the following positions: B1 (M or L), B2 (P, T, G or S), B3 (N, G, R or T), B4 (I, N or F), B5 (P, I, L or G), B6 (A, D, T or V) and B7 (R, I, M or G). In one embodiment, a HVR-H1 variant comprises 1-5 (1, 2, 3, 4 or 5) substitutions in any combination of the following positions: D3 (N, P, L, S, A, I), D5 (I, S or Y), D6 (G, D, T, K, R), D7 (F, H, R, S, T or V) and D9 (M or Y). In one embodiment, a HVR-H2 variant comprises 1-4 (1, 2, 3 or 4) substitutions in any combination of the following positions: E7 (Y), E9 (I), E10 (I), E14 (T or Q), E15 (D, K, S, T or V), E16 (L), E17 (E, H, N or D) and E18 (Y, E or H). In one embodiment, a HVR-H3 variant comprises 1-5 (1, 2, 3, 4 or 5) substitutions in any combination of the following positions: F1 (T, S), F3 (R, S, H, T, A, K), F4 (G), F6 (R, F, M, T, E, K, A, L, W), F7 (L, I, T, R, K, V), F8 (S, A), F10 (Y, N) and F11 (Q, S, H, F). Letter(s) in parenthesis following each position indicates an illustrative substitution (i.e., replacement) amino acid; as would be evident to one skilled in the art, suitability of other amino acids as substitution amino acids in the context described herein can be routinely assessed using techniques known in the art and/or described herein. In one embodiment, a HVR-L1 comprises the sequence of SEQ ID NO:4. In one embodiment, F1 in a variant HVR-H3 is T. In one embodiment, F1 in a variant HVR-H3 is S. In one embodiment, F3 in a variant HVR-H3 is R. In one embodiment, F3 in a variant HVR-H3 is S. In one embodiment, F7 in a variant HVR-H3 is T. In one embodiment, an antibody of the invention comprises a variant HVR-H3 wherein F1 is T or S, F3 is R or S, and F7 is T.

In one embodiment, an antibody of the invention comprises a variant HVR-H3 wherein F1 is T, F3 is R and F7 is T. In one embodiment, an antibody of the invention comprises a variant HVR-H3 wherein F1 is S. In one embodiment, an antibody of the invention comprises a variant HVR-H3 wherein F1 is T, and F3 is R. In one embodiment, an antibody of the invention comprises a variant HVR-H3 wherein F1 is S, F3 is R and F7 is T. In one embodiment, an antibody of the invention comprises a variant HVR-H3 wherein F1 is T, F3 is S, F1 is T, and F8 is S. In one embodiment, an antibody of the invention comprises a variant HVR-H3 wherein F1 is T, F3 is S, F7 is T, and F8 is A. In some embodiments, said variant HVR-H3 antibody further comprises HVR-L1, HVR-L2, HVR-L3, HVR-H1 and HVR-H2 wherein each comprises, in order, the sequence depicted in SEQ ID NOs:4, 5, 6, 20 and 21. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human id light chain framework consensus sequence.

In one embodiment, an antibody of the invention comprises a variant HVR-L2 wherein B6 is V In some embodiments, said variant HVR-L2 antibody further comprises HVR-L1, HVR-L3, HVR-H1, HVR-H2 and HVR-H3, wherein each comprises, in order, the sequence depicted in SEQ ID NOs:4, 6, 20, 21 and 22. In some embodiments, said variant HVR-L2 antibody further comprises HVR-L1, HVR-L3, HVR-H1, HVR-H2 and HVR-H3, wherein each comprises, in order, the sequence depicted in SEQ ID NOs:4, 6, 20, 21 and 23. In some embodiments, said variant HVR-L2 antibody further comprises HVR-L1, HVR-L3, HVR-H1, HVR-H2 and HVR-H3, wherein each comprises, in order, the sequence depicted in SEQ ID NOs:4, 6, 20, 21 and 24. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human id light chain framework consensus sequence.

In one embodiment, an antibody of the invention comprises a variant HVR-H2 wherein E14 is T, E15 is K and E17 is E. In one embodiment, an antibody of the invention comprises a variant HVR-H2 wherein E17 is E. In some embodiments, said variant HVR-H3 antibody further comprises HVR-L1, HVR-L2, HVR-L3, HVR-H1, and HVR-H3 wherein each comprises, in order, the sequence depicted in SEQ ID NOs:4, 5, 6, 20 and 22. In some embodiments, said variant HVR-H2 antibody further comprises HVR-L1, HVR-L2, HVR-L3, HVR-H1, and HVR-H3, wherein each comprises, in order, the sequence depicted in SEQ ID NOs:4, 5, 6, 20 and 23. In some embodiments, said variant HVR-H2 antibody further comprises HVR-L1, HVR-L2, HVR-L3, HVR-H1, and HVR-H3, wherein each comprises, in order, the sequence depicted in SEQ ID NOs:4, 5, 6, 20 and 24. In some embodiments, these antibodies further comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment of these antibodies, these antibodies further comprise a human κI light chain framework consensus sequence.

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following are examples of the methods and compositions of the invention. It is understood that various other embodiments may be practiced, given the general description provided above. The examples are offered for illustrative purposes only, and are not intended to limit the scope of the present invention in any way.

EXAMPLES

Materials and Methods

Cell Culture

Cell lines were obtained from American Type Culture Collection (ATCC), NCI Division of Cancer Treatment and Diagnosis tumor repository, or Japanese Health Sciences Foundation. All cell lines with the exception of 293 and Rat 1A were maintained in RPMI 1640 supplemented with 10% FBS (Sigma), penicillin/streptomycin (GIBCO), and 2 mM L-glutamine. 293 and Rat 1A cells were maintained in high glucose DMEM and supplemented as described.

Plasmids and Stable Cell Lines

Full-length Met WT-V5/His was described previously (Kong-Beltran M et al., Cancer Cell 6(1):75-84 (July 2004). Met WT-V5/His served as a template to produce a Y1003F point mutation using primers described previously (Peschard et al, 2001) via QuikChange Site-Directed Mutagenesis (Stratagene) according to the manufacturer's instructions. Exon 14 was deleted by using two sets of primers creating new NheI restriction sites flanking Met exon 14 (aa 963-1011) via QuikChange Site-Directed Mutagenesis and then digesting with NheI followed by religation of the plasmid. Mutations were verified by DNA sequencing. To generate Met stable cell lines in Rat 1A cells, 10 μg of each pRK5TKneo, Met WT-V5/His, Met Y1003F-V5/His, or Met ΔEx14-V5/His DNA was digested with KpnI and purified (Qiagen). Rat 1A cells were transfected with 4 μg of each DNA in a 6-well plate via Lipofectamine 2000 (Invitrogen) according to the manufacturer's instructions. The next day cells were trypsinized and seeded into 10 cm plates. Twenty-four hours later 500 μg/ml G418 (Sigma) was added. Selection continued for approximately two weeks before selecting Met-positive clones by FACS using 3D6 antibody (see U.S. Pat. No. 6,099,841) and PE staining. One cell was dropped per well. Expanded clones were lysed and tested for Met via immunoblotting with V5 antibody (Invitrogen).

Immunoprecipitation and Western Blot Analysis

For protein expression analyses in frozen tissue specimens, tissue (~100 mg) was homogenized in 200 μl of cell lysis buffer (Cell Signaling), containing protease inhibitor cocktail (Sigma), phosphatase inhibitor cocktails I and II (Sigma), 50 mM sodium fluoride, and 2 mM sodium orthovanadate using a Polytron® homogenizer (Kinematica). Samples were further lysed by gentle rocking for 1 hour at 4° C., prior to preclearance with a mixture of Protein A Sepharose Fast Flow (Amersham) and Protein G Sepharose 4 Fast Flow (Amersham). Protein concentrations were determined using Bradford reagent (BioRad). Proteins (20 μg) were subsequently resolved by SDS-PAGE, transferred to nitrocellulose membrane, and immunoblotted with Met (DL-21, Upstate) or β-actin (I-19, Santa Cruz) antibodies. Proteins were visualized by enhanced chemilluminescence (ECL Plus, Amersham). For coimmunoprecipitation studies involving transfected Met and Cbl, 3 μg of each Met construct and 3 μg of Cbl-flag were transfected into 293 cells using FuGENE6 (Roche). The next day cells were stimulated with 100 ng/ml rhuHGF for 30 minutes prior to harvest using 1% NP40 lysis buffer [50 mM Tris (pH 7.45), 150 mM NaCl, and 1% Nonidet 40] containing Complete protease inhibitor cocktail tablet (Roche) and phosphatase inhibitor cocktail II. Cell debris was centrifuged and 1 mg of lysates was immunoprecipitated with either 1.5 µl V5 (Invitrogen) or 2 µg Cbl (C-15, Santa Cruz) antibodies at 4° C. with rotation overnight followed by incubation with Protein G or A beads for 2 hrs. 2× sample buffer (Invitrogen) containing 20 mM DTT (Sigma) was added and samples were boiled for 5 minutes. Samples were loaded into 4-12% Tris-glycine gels (Invitrogen) and transferred to 0.45 µm nitrocellulose membranes (Invitrogen). The membrane was blocked with 5% non-fat milk for 1 hr followed by immunoblotting with V5, flag polyclonal (Sigma), or P-Tyr (4G10, Upstate) antibodies. For binding studies containing endogenous Cbl, 293 cells were transfected with 6 µg of each DNA construct per 10 cm plate using FuGENE6. The next day cells were stimulated with 100 ng/ml rhuHGF for 30 minutes prior to harvest. Samples were immunoprecipitated with 2 µg Cbl or 1.5 µg V5 antibodies, followed by immunoblotting with V5 or Cbl antibodies. The V5 immunoprecipitated blot was stripped using Restore western blot stripping buffer (Pierce) and reprobed with P-Met Y1003 (Biosource), P-Met Y1234/Y12345 (Cell Signaling), P-Met Y1349 (Cell Signaling), or P-Met 1365 (Biosource). For degradation studies, 293 cells were transfected with 0.25 µg of pRKSTKneo, Met WT-V5/His, Met Y1003F-V5/His, or Met ΔEx14-V5/His mutant using FuGENE6 in a 6-well plate. The next day cells were treated with 10 µg/ml cycloheximide (Sigma) for the indicated times. Lysates were analyzed by SDS-PAGE and the membrane was immunoblotted with V5 or actin antibodies.

Ubiquitination Assay 293 cells were transfected with 3 µg Met constructs, 2 µg Cbl-flag, 1 µg HA-ubiquitin, and pRKSTKneo or pFlag5a empty vectors when necessary to have 6 µg total DNA per sample using FuGENE6. The next day cells were treated with 25 µM MG-132 (Calbiochem) for 4 hours before harvesting. Cells were lysed in 1% NP-40 lysis buffer containing inhibitors, 25 µM MG-132, and 10 mM N-ethylmaleimide. Lysates (1 mg) were immunoprecipitated with 1.5 µg V5 antibody and immunoblotted with ubiquitin (P4D1, Santa Cruz) antibody and then stripped and reprobed with V5 antibody.

Cell Signaling and Inhibition Studies

To examine the prolonged signaling in H226, H596, H358, or Rat 1A-Met stable clones, the cells were rinsed with PBS then serum-starved in RPMI or DMEM media containing 0.5% BSA, 2 mM glutamine, and penicillin/streptomycin for one hour. rhuHGF or the agonistic anti-Met monoclonal antibody, 3D6 (Genentech), was added to the serum-free media for 10 minutes. The monolayer of cells was then rinsed with PBS and incubated with serum-free media until their extraction at the indicated times. Cells were then rinsed once with PBS, lysed with 1× SDS sample buffer containing 1× DTT (Invitrogen), sonicated briefly, and boiled for 5 minutes. To analyze Met receptor inhibition, serum-starved cells had anti-Met 5D5 antibody added to serum-free media at indicated concentrations for 30 minutes. Cells were then stimulated for 15 (for Met activation analysis) or 30 minutes (for Akt and MAPK analyses) with 100 ng/ml rhuHGF and lysed with 1× SDS sample buffer containing DTT. Boiled samples were analyzed by SDS-PAGE and immunoblotted with P-Met (Y1230Y11234/Y1235, BioSource), P-Met (Y1234/Y1235), Met (DL-21), P-MAPK (E10, Cell Signaling), P-MAPK (Cell Signaling), P-Akt (587F11, Cell Signaling); or Akt (Cell Signaling). Secondary antibodies used were anti-rabbit-AlexaFluor680 conjugated (Molecular Probes) or anti-mouse-IRDye800 conjugated (Rockland Immunochemicals). Proteins transferred onto nitrocellulose membranes were detected by infrared scan using Odyssey (LiCor) according to the manufacturer's recommended western blotting instructions followed by quantification. For cell viability assays, cells were plated in triplicate at ~1×10⁴ cells per well in 96-well plates in RPMI containing 0.5% FBS (assay medium) overnight, prior to stimulation with assay medium containing 50 ng/ml rhuHGF. Assay medium without rhuHGF was added to unstimulated wells. After 72 hrs, cell viability was measured using the Celltiter-Glo Luminescent Cell Viability Assay (Promega). Stimulation indices were determined by dividing the average cell viability units of HGF-stimulated cultures by the average cell viability units of unstimulated cultures. Average stimulation indices were determined from a minimum of 3 separate experiments. Growth inhibition assays were carried out in a similar manner, with either OA-5D5 or a control Ig added at the time of HGF stimulation.

In vivo Xenograft Model

Female athymic nude mice (Charles River, Hollister) were inoculated subcutaneously with pools of Rat1A stable cell lines expressing Met WT, Met Y1003F, Met ΔEx14, or vector control (5 million cells/mouse, n=5). 10 mg/kg anti-Met 3D6 agonist antibody which recognizes only human Met was administered for Met receptor stimulation, intra peritoneally, once weekly. Tumors were measured twice weekly using a digital caliper and tumor volumes were calculated using the following equation: Tumor Volume (mm3)=(π/6)(A)(B)(B). A=longest width; B=shortest width.

Results and Discussion

We sequenced all coding exons of Met from a panel of lung and colon tumor specimens representing primary tumors, tumor cell lines, and primary tumor xenograft models. In our sequencing effort, we identified somatic heterozygous mutations in primary lung tumor specimens in the intronic regions flanking exon 14 (FIG. 1). These mutations were tumor-specific and were not identified in non-neoplastic lung tissue from the same individuals (data not shown). In H596, a non-small cell lung cancer (NSCLC) cell line, we identified a homozygous point mutation in the 3p splice donor site. The presence of mutations within the dinucleotidic splice site consensus and the upstream polypyrimidine tract of exon 14, combined with the observation that exon 13 and exon 15 remained in-phase, suggested that a potential Met transcript lacking exon 14 could still produce a functional Met protein. To address this, we first performed RT-PCR amplification of Met RNA from the mutant tumors and cell line. All three intronic mutations resulted in a transcript of shorter length compared to the wildtype, consistent with deletion of exon 14 (data now shown). We also confirmed the absence of exon 14 by sequencing the RT-PCR products and our results showed an in-frame deletion that removes amino acids L964 through D1010 of Met. Interestingly, the mutant form of the receptor is the most predominantly expressed form, despite the tumor samples being heterozygous for the exon 14 deletion (data not shown), indicating a preferential expression of the variant transcript. This was further confirmed by Western blotting demonstrating the predominant expression of a truncated Met protein. Specimens harboring these intronic mutations were wildtype for K-ras, B-raf, EGFR, and HER2 in relevant exons sequenced (data not shown). Taken together, these results indicate the dominant nature of these Met intronic mutations mutations. Interestingly, a splice variant of Met lacking exon14 has been previously reported in normal mouse tissue, although the functional consequence with respect to tumorigenesis was unclear (20, 21). However, we did not detect expression of this splice variant in any normal human lung specimens examined (data not shown). The lack of this splice variant in normal human tissue has been additionally substantiated, as previously discussed (21). cDNA comprising a splice variant lacking exon 14 has been reported in a primary human NSCLC specimen; however the role of somatic mutagenesis in mediating splicing defects was not assessed, nor was the functional consequence, if any, of any mutant c-met that might have been expressed (22). Since nucleic acids comprising splice variants are not uncommon in cancer cells, the functional relevance of the reported splice variant was unknown.

The 47 amino acid deletion of exon 14 within the juxtamembrane domain of Met (L964-D1010) removes the Y1003 phosphorylation site necessary for Cbl binding and down regulation of the activated receptor. Previous studies show that a Y1003F mutation abolishes Cbl binding and maintains Met activation (6). We first confirmed loss of Cbl binding of the tumor-associated mutant Met by coimmunoprecipitation studies. 293 cells were transfectd with wildtype Met (Met WT), mutant Met Y1003F (Met Y1003F), and exon14 deleted Met (Met ΔEx14) by transfection of these Met constructs with Cbl-flag into 293 cells. We observed that Cbl binding to Met ΔEx14 is decreased compared to WT Met (FIG. 2A) and confirmed loss of Cbl binding to Met Y1003F (6). Cbl tyrosine phosphorylation by Met WT and Met mutants were equivalent, indicating that the Met mutations did not alter overall Cbl phosphorylation. Our data also indicated that Met WT coimmunoprecipitates with endogenous Cbl, but not with Met ΔEx14 (FIG. 2B) which is consistent with the observed co-expression of Met and Cbl. In addition, we examined tyrosine phosphorylation sites necessary for Met receptor activation. Our data indicate that phosphorylation of Y1234/Y1235, Y1349, and Y1365 is maintained in both Met WT and Met ΔEx14 (FIG. 2B). As expected, a loss of Y1003 phosphorylation in Met ΔEx14 was observed in contrast to Met WT (FIG. 2B). Since Cbl E3-ligase activity is reported to facilitate ubiquitin-mediated degradation of the receptor (6, 8), ubiquitination assays were carried out on cells transfected with Met WT, Met Y1003F and Met ΔEx14. Both Met ΔEx14 and Met Y1003F show attenuated ubiquitination compared to Met WT in the presence of Cbl (FIG. 2C). We confirmed that phosphorylation of Y1234/Y1235 was maintained in all Met constructs and phospho-Y1003 was lost in the mutants as before (data not shown). Interestingly, less processed Met WT was detected with Cbl co-expression compared to the mutants or expression of Met WT alone (FIG. 2C). These observations suggest that Met WT that binds Cbl is preferentially ubiquitinated and degraded (6, 24) in contrast to the Met ΔEx14. To determine if decreased ubiquitination of Met ΔEx14 leads to receptor down regulation, cells were transfected with Met constructs and treated with cycloheximide to block new protein synthesis. Met ΔEx14 showed delayed receptor down regulation over time compared to Met WT (FIG. 2D). The Met Y1003F mutant showed similar results (data not shown). Significantly, primary tumors harboring the exon 14 splice variant exhibited elevated levels of Met protein relative to both the patient-matched, normal adjacent lung tissue and Met wild-type adenocarcinomas (data not shown), despite expressing equivalent levels of Met at the transcript level. Furthermore, immunohistochemistry analysis of Met expression in these exon 14-deleted patient tumors reveals strong membranous expression in all neoplastic cells; in contrast, sporadic Met expression is observed in tumors with Met WT and in normal adjacent tissues (data not shown).

To determine if decreased down regulation of Met ΔEx14 affected downstream cell signaling upon HGF stimulation, Met, Akt, and MAPK phosphorylation levels were examined in NSCLC tumor cell lines harboring the exon 14 deletion (H596) or Met WT (H226 and H358). H596 cells showed that both phospho-Met and phospho-MAPK levels were maintained up to 3 hours post-HGF stimulation whereas both H226 and H358 cell lines, which expressed Met WT receptor, exhibited a steady loss of phosphorylation over time (FIG. 2E). Interestingly, phospho-Akt levels were not sustained over time despite initial activation in response to HGF. Phosphorylation of Stat3 and Stat5 were also examined, but did not exhibit elevated activation (data not shown). Since these tumor cell lines were derived from different genetic backgrounds, we generated stable cell lines in Rat1A cells with empty vector, Met WT, and Met ΔEx14 for comparison. Rat1A Met ΔEx14 demonstrated prolonged MAPK phosphorylation, but not Akt activation, compared to Met WT upon stimulation with the Met agonist 3D6 which activates the recombinant human receptor alone (25) (FIG. 2F, 5), corroborating data obtained from the NSCLC tumor cell lines.

The consequences of sustained Met and MAPK signaling was examined in HGF-mediated proliferation of H596 cells which harbor exon 14 deleted Met in the context of a panel of 28 additional NSCLC cell lines (FIG. 3A). H596 cells consistently exhibited the highest proliferative potential upon HGF stimulation in this panel of NSCLC cell lines. Moreover, to assess in vivo growth of the Met deletion, mice were inoculated with Rat 1A Met ΔEx14 stable cell lines and compared with Rat 1A Met WT for the ability to form tumors. Increased cell proliferation was observed in both Met ΔEx14 and Met Y1003F Rat1a cells compared with Met WT (data not shown). Upon stimulation with 3D6, the Rat 1A Met ΔEx14 cells were highly tumorigenic and developed larger tumors compared to that of Rat 1A Met WT (FIG. 3B). These results were consistent with an enhanced oncogenic role for the exon 14 deleted Met.

To determine whether Met antagonists could inhibit tumor cells harboring the Met deletion, H596 cells were treated with a known anti-c-met inhibitor (also referred to as anti-Met OA-5D5 (26)). Anti-Met OA-5D5 is an antibody comprising 3 immunoglobulin polypeptides—an intact light chain and heavy chain comprising variable domain sequences (shown in FIG. 9), and an N-terminally truncated heavy chain comprising an Fc portion that dimerizes with the Fc portion of the full length heavy chain. Construction and generation of anti-Met OA-5D5 is also described in PCT Pat. Appl. No. PCT/US2004/042619 (filed Dec. 17, 2004). Met and MAPK phosphorylation decreased with the addition of anti-Met OA-5D5 in a dose-dependent manner (FIG. 4A, 6). In addition, treatment of H596 cells with OA-5D5 resulted in the dose-dependent inhibition of cell proliferation in a ligand-dependent manner (FIG. 4B). These results support a therapeutic approach comprising targeting cancers expressing c-met that is hyperstabilized (such as a mutant c-met that exhibits deletion of the juxtamembrane) with a Met antagonist.

Despite the intrinsic nature of aberrant splicing in tumor cells, it is rather unexpected that a tumor-associated splice variant actually encodes a mutant receptor protein that is slower to be degraded intracellularly and that exhibits increased oncogenic activity. Our data strongly suggest that a splicing event, driven for example by somatic mutagenesis, is utilized by tumors to activate an oncogenic gene product. In the instant study, the identification of multiple types of intronic mutations that differentially affect the assembly of the spliceosome and selectively exclude exon 14, highlights the relevance of such a mutagenic event in Met. Interestingly, deletions and insertions within the juxtamembrane domain apparently play a role in the activation of certain receptor tyrosine kinases by altering receptor conformation and activation of the kinase domain (Hubbard, Nature Rev Mol Cell Bio. 5:464-470 (June 2004). Juxtamembrane deletion of KIT (Hirota et al., Science 279(5350):577-580 (Jan. 23, 1998) and PDGFRα (Heinrich, MC. et al Science 299:708, 2003) has been identified in gastrointestinal stromal tumors; internal tandem repeats within the juxtamembrane activate FLT3 in acute myeloid leukemia (Nakao, M et al Leukemia 10:1911, 1996). However, our identification of a juxtamembrane deletion herein characterizes a completely different mechanism of Met activation that delays receptor down regulation, thus resulting in mutant c-met proteins with significantly enhanced stability in cancer cells. These data suggest that mutations that drive receptor down regulation may lead to oncogenic activation and drive tumor development.

PARTIAL LIST OF REFERENCES

1. L. Trusolino, P. M. Comoglio, *Nat Rev Cancer* 2, 289 (April, 2002).
2. C. Birchmeier, W. Birchmeier, E. Gherardi, G. F. Vande Woude, *Nat Rev Mol Cell Biol* 4, 915 (December, 2003).
3. C. Ponzetto et al., *Cell* 77, 261 (Apr. 22, 1994).
4. K. M. Weidner et al., *Nature* 384, 173 (Nov. 14, 1996).
5. G. Pelicci et al., *Oncogene* 10, 1631 (Apr. 20, 1995).
6. P. Peschard et al., *Mol Cell* 8, 995 (November, 2001).
7. P. Peschard, N. Ishiyama, T. Lin, S. Lipkowitz, M. Park, *J Biol Chem* 279, 29565 (Jul. 9, 2004).
8. A. Petrelli et al., *Nature* 416, 187 (Mar. 14, 2002).
9. K. Shtiegman, Y. Yarden, *Semin Cancer Biol* 13, 29 (February, 2003).
10. M. D. Marmor, Y. Yarden, *Oncogene* 23, 2057 (Mar. 15, 2004).
11. P. Peschard, M. Park, *Cancer Cell* 3, 519 (June, 2003).
12. J. M. Siegfried et al., *Ann Thorac Surg* 66, 1915 (December, 1998).
13. P. C. Ma et al., *Anticancer Res* 23, 49 (January-February, 2003).
14. B. E. Elliott, W. L. Hung, A. H. Boag, A. B. Tuck, *Can J Physiol Pharmacol* 80, 91 (February, 2002).
15. C. Seidel, M. Borset, H. Hjorth-Hansen, A. Sundan, A. Waage, *Med Oncol* 15, 145 (September, 1998).
16. G. Maulik et al., *Cytokine Growth Factor Rev* 13, 41 (February, 2002).
17. R. Wang, L. D. Ferrell, S. Faouzi, J. J. Maher, J. M. Bishop, *J Cell Biol* 153, 1023 (May 28, 2001).
18. L. Schmidt et al., *Nat Genet* 16, 68 (May, 1997).
19. M. Jeffers et al., *Proc Natl Acad Sci USA* 94, 11445 (Oct. 14, 1997).
20. C. C. Lee, K. M. Yamada, *J Biol Chem* 269, 19457 (Jul. 29, 1994).
21. C. M. Baek, S. H. Jeon, J. J. Jang, B. S. Lee, J. H. Lee, *Exp Mol Med* 36, 283 (Aug. 31, 2004).
22. P. C. Ma et al., *Cancer Res* 65, 1479 (Feb. 15, 2005).
23. P. C. Ma et al., *Cancer Res* 63, 6272 (Oct. 1, 2003).
24. M. Jeffers, G. A. Taylor, K. M. Weidner, S. Omura, G. F. Vande Woude, *Mol Cell Biol* 17, 799 (February, 1997).
25. K. Ohashi et al., *Nat Med* 6, 327 (March, 2000).
26. Schwall et al., Proceedings of the American Association for Cancer Research (Abstract #1424) 45:327 (March 2004).

The invention claimed is:

1. A method of treating a lung tumor in a subject, said method comprising administering a c-met antagonist to a subject, whereby the tumor is treated, wherein the lung tumor comprises hyperstabilized human c-met polypeptide comprising a deletion of amino acids L964 to D1010 of SEQ ID NO:17 such that c-met degradation is diminished compared to wild type c-met, wherein the hyperstabilized c-met polypeptide binds c-met ligand and has c-met signaling activity, and wherein the c-met antagonist is a c-met antagonist antibody that inhibits c-met signaling activity of the hyperstabilized c-met polypeptide.

2. The method of claim 1, wherein the tumor is determined to comprise the hyperstabilized c-met polypeptide.

3. The method of claim 1, wherein the tumor is determined to comprise mutant c-met transcript comprising deletion of at least a portion of exon 14.

4. The method of claim 1, wherein the c-met antagonist antibody is a monovalent antibody.

5. The method of claim 1, wherein the c-met antagonist antibody is a humanized, human or chimeric antibody.

6. The method of claim 2, wherein c-met polypeptide is detected.

7. The method of claim 2, wherein c-met polynucleotide is detected.

* * * * *

UNITED STATES PATENT AND TRADEMARK OFFICE
CERTIFICATE OF CORRECTION

PATENT NO. : 7,615,529 B2
APPLICATION NO. : 11/388757
DATED : November 10, 2009
INVENTOR(S) : Kong-Beltran et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 142 days.

Signed and Sealed this

Nineteenth Day of October, 2010

David J. Kappos
*Director of the United States Patent and Trademark Office*